US006406886B1

(12) United States Patent
Minato et al.

(10) Patent No.: US 6,406,886 B1
(45) Date of Patent: Jun. 18, 2002

(54) DNA ENCODING SPA-1PROTEIN

(75) Inventors: Nagahiro Minato, Kyoto; Masakazu Hattori, Nagaokakyo; Hiroshi Kubota, Kyoto; Masatsugu Maeda, Tokorozawa, all of (JP)

(73) Assignee: Nagahiro Minato, Kyoto (JP)

( * ) Notice: Subject to any disclaimer, the term of this patent is extended or adjusted under 35 U.S.C. 154(b) by 0 days.

(21) Appl. No.: 08/895,810

(22) Filed: Jul. 17, 1997

Related U.S. Application Data

(60) Division of application No. 08/380,403, filed on Jan. 30, 1995, now Pat. No. 5,831,024, which is a continuation-in-part of application No. 08/325,909, filed on Oct. 19, 1994, now abandoned.

(30) Foreign Application Priority Data

May 30, 1994 (JP) ............................................. 6-139513
Oct. 20, 1994 (JP) ............................................. 6-279712

(51) Int. Cl.$^7$ ........................ C12N 15/12; C12N 15/63; C12N 15/85

(52) U.S. Cl. ................... 435/69.2; 435/325; 435/252.3; 435/320.1; 536/23.5; 536/23.1; 536/24.1

(58) Field of Search ............................... 536/23.5, 23.1, 536/24.1; 435/320.1, 69.1, 69.2, 325, 252.3

(56) References Cited

PUBLICATIONS

Rubin Feld et al. Cell 65 (1991) 1033–1042.*
Rudinger, "Peptide Hormones", (ed. J.A. Parsons) University Park Press, Baltimore, Jun. 1976, p. 1–7.

* cited by examiner

Primary Examiner—Gary L. Kunz
Assistant Examiner—Robert C. Hayes
(74) Attorney, Agent, or Firm—Foley & Lardner

(57) ABSTRACT

A cell division mechanism controlling protein which is not expressed in the interphase but is expressed in the nucleus after entering into a cell cycle, in the cell cycle of mammalian cell, and fragments thereof, as well as DNAs coding for said protein or fragments thereof, as well as antibodies against said protein or fragment thereof.

19 Claims, 9 Drawing Sheets

Fig. 1

```
SpanN   -7  GQGSRRRNYN NQEAGAAFMQ FLTLLGDVVR LKGFESYRAQ LDTKTDSTGT HSLYTTYQDH
            **.:***..   .*..:.      **..*.     *...*.    ***        .*.*
GAP3m  203  GQTSEEELFS TNEESPAFVE FLEFLGQKVK LQDFXGFRGG LDVTHGQTGT ESVYCNFRNK SpanN   54  EIMFHVSTML PYTPNNQQQL LRKRHIGNDI VTIVFQEPGS KPFCPTTIRS HFQHVFLVVR
            *******.  *  ..:*  ********* *..*.*:*    *  *....    *  *..*:.
GAP3m  263  EIMFHVSTKL PYTEGDAQQL QRKRHIGNDI VAVVFQD-EN TPFVPDMIAS NFLHAYVVVQ SpanN  114  AHAPCTPHTS YRVAVSRTQD TPAFGPALPE GGGPFAANAD FRAFLLAKAL NGEQAAGHAR
            *.:..    .  *.*.*..*   *.*..    *.*      *.****.*.*  *
GAP3m  413  AEGGGPDGPL YKVSVTARDD VPFFGPPLPD -PAVFRKGPE FQEFLLTKLI NAEYACYKAE SpanN  174  QFHAMATRTR QQYLQDLATN EVTTTSLDSA SRFGLPSLGG RRRATPRSPG ADVQAAGALM
            .* ..:**:*  ..* *  .*
GAP3m  473  KFAKLEERTR AALETLYEE  LHIHSQSMMG LGGDEDKMEN GSGGGGFFES FKRVIRSRSQ
```

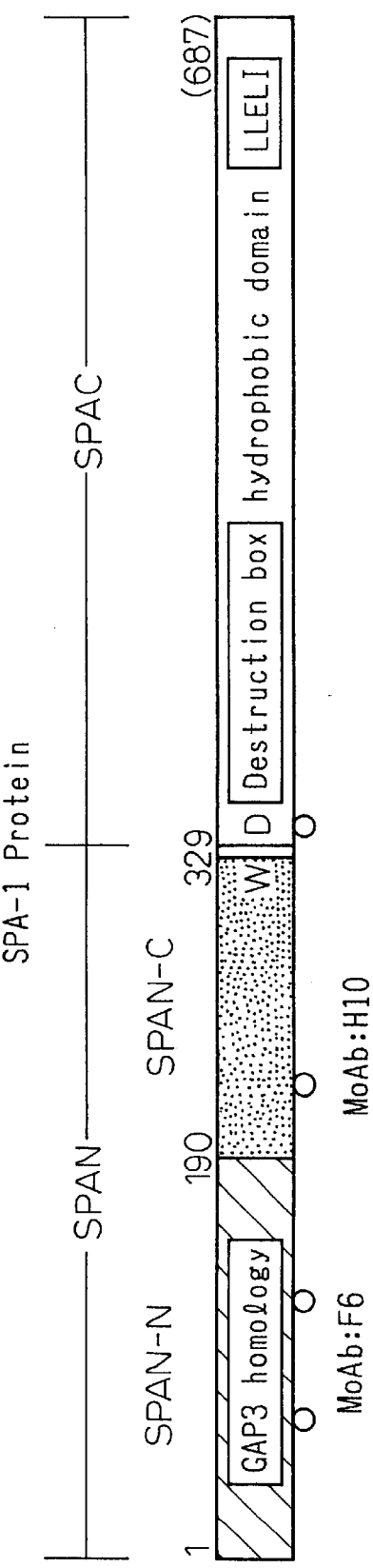

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 3519 base pairs
      (B) TYPE: nucleic acid
      (C) STRANDEDNESS: double
      (D) TOPOLOGY: linear (ii) MOLECULE TYPE: DNA (genomic)

(ix) FEATURE:
    (A) NAME/KEY: CDS
    (B) LOCATION: 1200..3278

(xi) SEQUENCE DESCRIPTION: SEQ ID NO: 1:

```
GTCCTGCATG CAGCTGCCCC AGGAGCTCCT GTGTCCTTGA GGCCCATCTG A ACAGCCCCC      60

TCCTCTGCAG TGCAGAAACC ACTGAAGCCT CAGCCTTCTG GGTGGGCACC A AGGACCCGT     120

GCCCACCAAT GCGGCCCGGC CCCCAGAGAG TCAGGCCCAC AGGAGCACGC C CATGTGGGC     180

CGGAGGTGTG GGGAGCCCTC GGCGGGCATG GCCCCTGCAC CTACCGATGA C CTCTTTGCC     240

CGTAAGCTTC GCCAACCTGC CCGGCCCCCA CTGACACCAC AATACCTTTG A GCCGAGGCC     300

AGCTCGGGGC CCACTCTTGC GCAGTGGCAG TGATGCTGGT GAAGTCCGGC C CCCTACACC     360

AGCCAGCCCC CGTGCCCGTG CCCACAGCCA CGAGGATGCC AGCCGCCCTG C TGCAACCCC     420

TACTCGGCTC TTCACTGACC CACTGGCACT GCTAGGGTTG CCAGCAGAAG A GCCAGAGCC     480

CACCTTCCCG CCAGTGCTGG AACCCCGGTG GTTTGCTCAC TATGATGTGC A GAGCTTGCT     540

CTTTGACTGG GCTCCACGAC CTCGGGGGAC AGGCAGCCAT ACAGAGGCAA A CTCTGGGAC     600

CTTAGCTGAG GGCCAGACTA CCACCTCAGA TCTACTGCTC GGGGCACCTG G CTTTGTGAG     660

CGAGCTTGGT GGTGAGGGTG AGCTAGGGCT GGGTGGGCCA ATATCCCCAC C TGTGCCCCC     720

TGCACTGCCT AATGCGGCTG TGTCCGTCCT GGAGGAGCCA CAGACCCGGA C CACACTTAC     780

AGCCTGGAGC ACGCAGATCT GGGTGCAGGC TACTACCGCA AGTACTTCTA T GGCAAAGAA     840

CACCAGAACT TCTTTGGGTT GGATGAGGCG CTGGGTCCGG TGGCCGTGAG C CTGCGACGG     900

GAGGAGAAAG AGGGCAGCGG AGGGGGCACC TACACAGCTA CCGGGTCATC G TGCGGACCA     960

CGCAGCTCCG GACCCTCCGT GGCACCATCT CGGAGGACGA ACTGCCTCCC G GCCCCCCGA    1020

GCGTATCTCC GAGGAAGCTT CTGGAACATG TGCTCCACGG CTGAGCCCAC C TGCCTGCGC    1080

CTGGGTTCAG CCTCTCCCAA GGTGCCCCGC AGCTGCTTAC TCTGGATGAG C AAGTGCTGA    1140

GCTTCCAACG CAAGGTGGGC ATCCTGTACT GCCGCGCAGG CCAGGGCTCT G AGGAAGAG    1199

ATG TAC AAC AAC CAG GAG GCC GGA GCA GCC T TT ATG CAG TTC CTT ACT       1247
Met Tyr Asn Asn Gln Glu Ala Gly Ala Ala P he Met Gln Phe Leu Thr
  1               5                  10                  15

TTG CTG GGT GAT GTG GTG CGA CTC AAA GGC T TT GAA AGT TAC CGG GCC       1295
Leu Leu Gly Asp Val Val Arg Leu Lys Gly P he Glu Ser Tyr Arg Ala
             20                  25                  30

CAG CTG GAT ACC AAA ACG GAT TCC ACG GGC A CA CAC TCA CTC TAC ACC       1343
Gln Leu Asp Thr Lys Thr Asp Ser Thr Gly T hr His Ser Leu Tyr Thr
         35                  40                  45

ACC TAC CAA GAC CAT GAG ATC ATG TTT CAC G TG TCC ACG ATG CTG CCT       1391
Thr Tyr Gln Asp His Glu Ile Met Phe His V al Ser Thr Met Leu Pro
     50                  55                  60

TAC ACG CCT AAT AAC CAG CAA CAG CTC CTG A GG AAG CGT CAT ATC GGC       1439
Tyr Thr Pro Asn Asn Gln Gln Gln Leu Leu A rg Lys Arg His Ile Gly
 65                  70                  75                  80

AAC GAT ATT GTG ACC ATC GTG TTC CAG GAG C CC GGT AGC AAG CCC TTC       1487
Asn Asp Ile Val Thr Ile Val Phe Gln Glu P ro Gly Ser Lys Pro Phe
                 85                  90                  95

TGC CCT ACA ACA ATC CGC TCT CAC TTC CAG C AC GTT TTC TTG GTG GTG       1535
Cys Pro Thr Thr Ile Arg Ser His Phe Gln H is Val Phe Leu Val Val
            100                 105                 110

CGT GCG CAT GCT CCC TGC ACC CCA CAC ACC T CA TAC AGG GTG GCA GTG       1583
Arg Ala His Ala Pro Cys Thr Pro His Thr S er Tyr Arg Val Ala Val
        115                 120                 125

AGC CGC ACC CAG GAC ACT CCT GCC TTC GGG C CT GCG CTG CCA GAA GGC       1631
```

```
Ser Arg Thr Gln Asp Thr Pro Ala Phe Gly P ro Ala Leu Pro Glu Gly
        130                 135                 140

GGA GGC CCC TTT GCA GCC AAT GCC GAT TTC C GG GCC TTT CTG TTG GCT    1679
Gly Gly Pro Phe Ala Ala Asn Ala Asp Phe A rg Ala Phe Leu Leu Ala
145                 150                 155                 160

AAG GCA CTC AAT GGT GAG CAA GCG GCT GGT C AT GCA CGC CAG TTC CAC    1727
Lys Ala Leu Asn Gly Glu Gln Ala Ala Gly H is Ala Arg Gln Phe His
            165                 170                 175

GCC ATG GCT ACA CGC ACA CGC CAA CAG TAC C TG CAG GAC CTG GCT ACT    1775
Ala Met Ala Thr Arg Thr Arg Gln Gln Tyr L eu Gln Asp Leu Ala Thr
                180                 185                 190

AAT GAA GTG ACC ACT ACT TCG CTG GAC TCG G CT TCG CGG TTT GGC CTG    1823
Asn Glu Val Thr Thr Thr Ser Leu Asp Ser A la Ser Arg Phe Gly Leu
            195                 200                 205

CCA TCT CTG GGG GGT AGG CGC CGG GCA ACC C CT CGG AGC CCA GGC GCG    1871
Pro Ser Leu Gly Gly Arg Arg Arg Ala Thr P ro Arg Ser Pro Gly Ala
        210                 215                 220

GAC GTA CAG GCG GCG GGT GCG CTG ATG TGG G GC GTA CGC GCG GCT CCA    1919
Asp Val Gln Ala Ala Gly Ala Leu Met Trp G ly Val Arg Ala Ala Pro
225                 230                 235                 240

GGG GCG CGG GTC GCA GCG GGA GCT GAA ACG A GC GGT CCG GAC GAC GCC    1967
Gly Ala Arg Val Ala Ala Gly Ala Glu Thr S er Gly Pro Asp Asp Ala
                245                 250                 255

GAG GTG CCC TGC TTG TTG GGC ATC TCA GCA G AG ACA CTG GTG CTG GTG    2015
Glu Val Pro Cys Leu Leu Gly Ile Ser Ala G lu Thr Leu Val Leu Val
            260                 265                 270

GCA CCT CGC GAC GGC CGC GTG GTC TTC AAT T GT GCC TGT CGC GAC GTA    2063
Ala Pro Arg Asp Gly Arg Val Val Phe Asn C ys Ala Cys Arg Asp Val
        275                 280                 285

TTG GCC TGG ACC TTC TCA GAG CAC CAA CTC G AT CTG TAC CAC GGG CGC    2111
Leu Ala Trp Thr Phe Ser Glu His Gln Leu A sp Leu Tyr His Gly Arg
        290                 295                 300

GGG GAG GCG ATC ACG CTG CGG CTC GAC GGG G CC CCA GGG CAA GCC GTG    2159
Gly Glu Ala Ile Thr Leu Arg Leu Asp Gly A la Pro Gly Gln Ala Val
305                 310                 315                 320

GGC GAA GTC GTG GCA CGT CTG CAG CTG GTG A GC CGC GGG TGT GAG ACC    2207
Gly Glu Val Val Ala Arg Leu Gln Leu Val S er Arg Gly Cys Glu Thr
                325                 330                 335

AGA GAA CTA GCG CTG CCC AGA GAT GGC CAA G GT CGC CTG GGC TTC GAG    2255
Arg Glu Leu Ala Leu Pro Arg Asp Gly Gln G ly Arg Leu Gly Phe Glu
            340                 345                 350

GTG GAT GCA GAA GGC TTC ATC ACG CAC GTG G AG CGC TTC ACG TTT GCG    2303
Val Asp Ala Glu Gly Phe Ile Thr His Val G lu Arg Phe Thr Phe Ala
        355                 360                 365

GAG ACC ACG GGG CTT CGG CCT GGA GCT CGT T TG CTG CGA GTC TGC GGC    2351
Glu Thr Thr Gly Leu Arg Pro Gly Ala Arg L eu Leu Arg Val Cys Gly
370                 375                 380

CAG ACG CTG CCC AAG CTG GGT CCC GAA GCT G CT GCC CAG ATG CTG CGC    2399
Gln Thr Leu Pro Lys Leu Gly Pro Glu Ala A la Ala Gln Met Leu Arg
385                 390                 395                 400

TCT GCG CCG AAG GTC TGC GTC ACG GTC CTA C CC CCA GAC GAG AGC GGC    2447
Ser Ala Pro Lys Val Cys Val Thr Val Leu P ro Pro Asp Glu Ser Gly
                405                 410                 415

CGG CCG CAG AGG AGC TTT TCG GAG CTC TAT A TG CTC TCT CTG AAG GAA    2495
Arg Pro Gln Arg Ser Phe Ser Glu Leu Tyr M et Leu Ser Leu Lys Glu
            420                 425                 430

CCC AGC CGG CGG GGG GGC CCA GAG CCA GTA C AG GAT GAA ACT GGG AAG    2543
Pro Ser Arg Arg Gly Gly Pro Glu Pro Val G ln Asp Glu Thr Gly Lys
        435                 440                 445
```

```
TTG GTC ATA TTG CCT CCC ACC AAG CAG CTG C TA CAT TTT TGC CTG AAA         2591
Leu Val Ile Leu Pro Pro Thr Lys Gln Leu L eu His Phe Cys Leu Lys
        450                 455                 460

GAC AGC AGC AGT CCT CCG GGG CCT GGG GAT C TG ACT GAG GAG AGG ACA         2639
Asp Ser Ser Ser Pro Pro Gly Pro Gly Asp L eu Thr Glu Glu Arg Thr
465                 470                 475                 480

GAG TTC CTG CGC AGC CAC AAC TCC CTG TCA T CT GGA AGC TCC CTG TCC         2687
Glu Phe Leu Arg Ser His Asn Ser Leu Ser S er Gly Ser Ser Leu Ser
                485                 490                 495

GAT GAG GCT CCA GTC CTG CCC AAC ACC ACT C CA GAC CTC CTC CTT GTC         2735
Asp Glu Ala Pro Val Leu Pro Asn Thr Thr P ro Asp Leu Leu Leu Val
        500                 505                 510

ACC ACT GCC AAC CCA TCT GCA CCT GGT ACT G AC AGA GAA ACA CCC CCT         2783
Thr Thr Ala Asn Pro Ser Ala Pro Gly Thr A sp Arg Glu Thr Pro Pro
        515                 520                 525

TCC CAG GAC CAG TCA GGA AGC CCC AGT AGC C AT GAA GAC ACC AGT GAC         2831
Ser Gln Asp Gln Ser Gly Ser Pro Ser Ser H is Glu Asp Thr Ser Asp
530                 535                 540

TCA GGC CCA GAA CTG AGG GCC TCC ATC CTG C CC AGA ACC TTG TCT CTG         2879
Ser Gly Pro Glu Leu Arg Ala Ser Ile Leu P ro Arg Thr Leu Ser Leu
545                 550                 555                 560

CGG AAT TCC ATC AGT AAG ATT ATG TCG GAA G CT GGC AGT GAG ACC CTG         2927
Arg Asn Ser Ile Ser Lys Ile Met Ser Glu A la Gly Ser Glu Thr Leu
                565                 570                 575

GAG GAT GAG TGG CAG TCC ATC TCA GAG ATC G CC TCC ACT TGC AAC ACA         2975
Glu Asp Glu Trp Gln Ser Ile Ser Glu Ile A la Ser Thr Cys Asn Thr
                580                 585                 590

ATT CTG GAG TCA CTG TCC CGG GAG GGA CAA C CC ATC TCA GAG AGC GGA         3023
Ile Leu Glu Ser Leu Ser Arg Glu Gly Gln P ro Ile Ser Glu Ser Gly
                595                 600                 605

GAC CCC AAG GAA GCT TTA AAG TGT GAT TCT G AG CCA GAA CCC GGG AGC         3071
Asp Pro Lys Glu Ala Leu Lys Cys Asp Ser G lu Pro Glu Pro Gly Ser
610                 615                 620

CTG TCA GAA AAG GTC TCT CAC CTA GAG TCC A TG CTC TGG AAG CTC CAG         3119
Leu Ser Glu Lys Val Ser His Leu Glu Ser M et Leu Trp Lys Leu Gln
625                 630                 635                 640

GAG GAC CTG CAG AGG GAG AAG GCG GAC AGG G CA GCC TTG GAG GAG GAG         3167
Glu Asp Leu Gln Arg Glu Lys Ala Asp Arg A la Ala Leu Glu Glu Glu
                645                 650                 655

GTT CGG AGC CTC AGA CAC AAC AAC CAG AGG C TG CTG GCA GAG TCC GAG         3215
Val Arg Ser Leu Arg His Asn Asn Gln Arg L eu Leu Ala Glu Ser Glu
                660                 665                 670

AGT GCC GCC ACC CGC CTG CTC CTG GCC TCT A AG CAT CTG GGT GCA CCC         3263
Ser Ala Ala Thr Arg Leu Leu Leu Ala Ser L ys His Leu Gly Ala Pro
                675                 680                 685

ACT ACT GAC CTG GCC TGAGTTCCAA TCTGAATCTG GACCTGCT TG GAACTGCCTG         3318
Thr Thr Asp Leu Ala
    690

GCCCCTCAGA GCAACTGGGT CATACTAGTG CCCTTCCTCA GGACTTCTTC C CTGCGCTGA       3378

GGCGCGTCTT AGCACTGCCC CCTCTTCCCA GCCCATTTGG TGGCTAATGC C TGTCCCTGT       3438

TTGTAAATAT CCTGTAAAGA AAAGGAGACA TCAGAGTTTA AAAAAAAGAA A CAACAAGAA       3498

GAAGCAAAAA AAAAAAAAA A                                                  3519

(2) INFORMATION FOR SEQ ID NO: 2:

(i) SEQUENCE CHARACTERISTICS:
        (A) LENGTH: 693 amino acids
        (B) TYPE: amino acid
        (D) TOPOLOGY: linear
```

(ii) MOLECULE TYPE: protein (xi) SEQUENCE DESCRIPTION: SEQ ID NO: 2:

Met Tyr Asn Asn Gln Glu Ala Gly Ala Ala Phe Met Gln Phe Leu Thr
 1               5                  10                  15

Leu Leu Gly Asp Val Val Arg Leu Lys Gly Phe Glu Ser Tyr Arg Ala
            20                  25                  30

Gln Leu Asp Thr Lys Thr Asp Ser Thr Gly Thr His Ser Leu Tyr Thr
            35                  40                  45

Thr Tyr Gln Asp His Glu Ile Met Phe His Val Ser Thr Met Leu Pro
50                      55                  60

Tyr Thr Pro Asn Asn Gln Gln Gln Leu Leu Arg Lys Arg His Ile Gly
65                  70                  75                  80

Asn Asp Ile Val Thr Ile Val Phe Gln Glu Pro Gly Ser Lys Pro Phe
                85                  90                  95

Cys Pro Thr Thr Ile Arg Ser His Phe Gln His Val Phe Leu Val Val
                100                 105                 110

Arg Ala His Ala Pro Cys Thr Pro His Thr Ser Tyr Arg Val Ala Val
            115                 120                 125

Ser Arg Thr Gln Asp Thr Pro Ala Phe Gly Pro Ala Leu Pro Glu Gly
130                 135                 140

Gly Gly Pro Phe Ala Ala Asn Ala Asp Phe Arg Ala Phe Leu Leu Ala
145                 150                 155                 160

Lys Ala Leu Asn Gly Glu Gln Ala Ala Gly His Ala Arg Gln Phe His
                165                 170                 175

Ala Met Ala Thr Arg Thr Arg Gln Gln Tyr Leu Gln Asp Leu Ala Thr
            180                 185                 190

Asn Glu Val Thr Thr Thr Ser Leu Asp Ser Ala Ser Arg Phe Gly Leu
            195                 200                 205

Pro Ser Leu Gly Gly Arg Arg Arg Ala Thr Pro Arg Ser Pro Gly Ala
            210                 215                 220

Asp Val Gln Ala Ala Gly Ala Leu Met Trp Gly Val Arg Ala Ala Pro
225                 230                 235                 240

Gly Ala Arg Val Ala Ala Gly Ala Glu Thr Ser Gly Pro Asp Asp Ala
                245                 250                 255

Glu Val Pro Cys Leu Leu Gly Ile Ser Ala Glu Thr Leu Val Leu Val
                260                 265                 270

Ala Pro Arg Asp Gly Arg Val Phe Asn Cys Ala Cys Arg Asp Val
                275                 280                 285

Leu Ala Trp Thr Phe Ser Glu His Gln Leu Asp Leu Tyr His Gly Arg
            290                 295                 300

Gly Glu Ala Ile Thr Leu Arg Leu Asp Gly Ala Pro Gly Gln Ala Val
305                 310                 315                 320

Gly Glu Val Val Ala Arg Leu Gln Leu Val Ser Arg Gly Cys Glu Thr
                325                 330                 335

Arg Glu Leu Ala Leu Pro Arg Asp Gly Gly Arg Leu Gly Phe Glu
                340                 345                 350

Val Asp Ala Glu Gly Phe Ile Thr His Val Glu Arg Phe Thr Phe Ala
            355                 360                 365

Glu Thr Thr Gly Leu Arg Pro Gly Ala Arg Leu Leu Arg Val Cys Gly
            370                 375                 380

Gln Thr Leu Pro Lys Leu Gly Pro Glu Ala Ala Ala Gln Met Leu Arg
385                 390                 395                 400

```
Ser Ala Pro Lys Val Cys Val Thr Val Leu Pro Pro Asp Glu Ser Gly
            405                 410                 415
Arg Pro Gln Arg Ser Phe Ser Glu Leu Tyr Met Leu Ser Leu Lys Glu
            420                 425                 430
Pro Ser Arg Arg Gly Gly Pro Glu Pro Val Gln Asp Glu Thr Gly Lys
            435                 440                 445
Leu Val Ile Leu Pro Pro Thr Lys Gln Leu Leu His Phe Cys Leu Lys
            450                 455                 460
Asp Ser Ser Ser Pro Pro Gly Pro Gly Asp Leu Thr Glu Arg Thr
465                 470                 475                 480
Glu Phe Leu Arg Ser His Asn Ser Leu Ser Ser Gly Ser Ser Leu Ser
            485                 490                 495
Asp Glu Ala Pro Val Leu Pro Asn Thr Thr Pro Asp Leu Leu Leu Val
            500                 505                 510
Thr Thr Ala Asn Pro Ser Ala Pro Gly Thr Asp Arg Glu Thr Pro Pro
            515                 520                 525
Ser Gln Asp Gln Ser Gly Ser Pro Ser Ser His Glu Asp Thr Ser Asp
            530                 535                 540
Ser Gly Pro Glu Leu Arg Ala Ser Ile Leu Pro Arg Thr Leu Ser Leu
545                 550                 555                 560
Arg Asn Ser Ile Ser Lys Ile Met Ser Glu Ala Gly Ser Glu Thr Leu
            565                 570                 575
Glu Asp Glu Trp Gln Ser Ile Ser Glu Ile Ala Ser Thr Cys Asn Thr
            580                 585                 590
Ile Leu Glu Ser Leu Ser Arg Glu Gly Gln Pro Ile Ser Glu Ser Gly
            595                 600                 605
Asp Pro Lys Glu Ala Leu Lys Cys Asp Ser Glu Pro Glu Pro Gly Ser
            610                 615                 620
Leu Ser Glu Lys Val Ser His Leu Glu Ser Met Leu Trp Lys Leu Gln
625                 630                 635                 640
Glu Asp Leu Gln Arg Glu Lys Ala Asp Arg Ala Ala Leu Glu Glu Glu
            645                 650                 655
Val Arg Ser Leu Arg His Asn Asn Gln Arg Leu Leu Ala Glu Ser Glu
            660                 665                 670
Ser Ala Ala Thr Arg Leu Leu Leu Ala Ser Lys His Leu Gly Ala Pro
            675                 680                 685
Thr Thr Asp Leu Ala
690

(2) INFORMATION FOR SEQ ID NO: 3:

(i) SEQUENCE CHARACTERISTICS:
        (A) LENGTH: 5687 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

GGATCCCAAA CTGAGGCAGC AGCCTCCTAG CCAGGCCCTA AGAGCAAAC C CATGGGCTG       60

GTCCCTCATT GGAGCCCATG GCCAGGACTG ACTTTGCCTC TGGGGCCTGC A CTGCCCCCA     120

AGGCTGGCCT CCTTAGCCTG GACCTGGGGC CCGATATGTG GCAAGGGTGG G TTCATTCGT     180

TCTTTTGTCA TTTTTCTTTC TTTTTTTTTC TGTGCTTCAG AGACACCAAA T TAATAACAC     240
```

-continued

```
TATTTTTGAT TTTGGTTGGC AGTTTTATTT TCTGTGGGAC GAGGTGAGGT T GGTAGAGGT      300
GCCGGAGGGA GGCTGAAGTC AGAAGAGTGT GAGGGATAAG GGGTCAGACT G CTGGGCTCC      360
AGGCAGACAT GAGGTGGGAT GGGCTGCCTT CCTCACCTGC CTCTGCCTTT C TTTTTTTTT      420
TTTTTTTTTT AATGGTTTAA GAGCTTATTA TAGAAATGCC AGTCGAGGGA A GAGAAAAGG      480
TAGAGAGAGA GAGTGTGTGG GACGGGGAAG GCTAGAGAAG AAGAAAGAGA A AGGAGAGAA      540
AAGACAAAGG GAAGAGGAGA AAGAAGTGAG AGGATAAAGG AGAGAGCTGA G CCTCTGCTT      600
TTCAAGCAGT CCTCTATCCC CAGGTGGCTC ACACATCCAT CAGCCTTGAT C TTATCAAAG      660
ACTGCTCAAC CTCATTTGTC CAAGCTTAAG AAAATAACAG GTGAATAGAA A GGATTCTAT      720
TCGTTTTTGA GACAGGGGCT TACCATGTAC TCCCTATGTA CATCAGGCTG G CCTTGACCT      780
CAGATCCACC TGCCTCTGCC TTCAGAGTGC TGGATTTAAT GGTGTTCGCC A TTGCATAAA      840
TGGTAGCCTG TGTAGATCAG TTATCTAGCT TGGCCCAGCC CTTAAAGAGT G AAATAGTTT      900
CTGGCCCTAA TACCTGCTGT CTGCTGAGCC ACAGCAGGAC ACTAAGTGGC C TCTAGCGCT      960
CCAATTGGTC TGGAAGGCAG GTACATTTGT TCCCATTTCT CGGTGAAGTC A CTGACTGGG     1020
CTAGGACCGG GAGTTAAAAG AGCAGCTGAA GGCTGGGACA GAGAACTTCA G GCTGTCCGG     1080
GGCTGCCTAG GTTCCTGTCG GAGGTCCCCA CCCACTGTGC TTCCGCCTTA G ACAGCTCCC     1140
GGGTAGTCCC GCCCCTCCAC TACGTACCGC CTCCATCCTG GCCCCGCCCC C AGGGAGGGA     1200
GGCGCCGGGA GCGGTGTGAG CAGGCAGCGG GACCTTGGTG CGGAAGGCAG C GGTGGCCAG     1260
CTTGAGCCCG AGAGGTACTG GCGGGATCAG GGATCGGGAG GCACCAGGTT C GGGCTGGAT     1320
ACCCAACAAA GTAGCCTGGA CGTGAACCCT GTAGTGTGGG GAGGAACGGG A CTATTGGCT     1380
GCTTTCGCTA CACGCACCCC ACCCAACCTC CTGCCCCAGT CCAGCCCCGA G TCAGCACGT     1440
CCAGTGTTCT GCTCCTGCTG GCAGCTCCCA CTCCCTCCTC TGCATGAGCA G ATTCAGAGC     1500
TCACTGAGTG GATTCATTGG TTCTGGACTT TTCTCAGCAA TGCTGGCGCA G CTGCTCCTG     1560
CTGCTGTTGT TGTTGTGGGG CTCCCCCTAT TCTGGGCTC CCCTGTTCCC A GTGTGACCT      1620
CTTTCCCAGC CTTTGCAATC CTGAGTCTGG CCTGGGAGGA AACATCTGCA G CACTCCCTG     1680
GCAACAGAAA TAGGGTCACG ACCTCCAGAT GTGCTGGGAA GCATCCAGCG C CTCCTCCTG     1740
GGGCAGCCAG GCCTTCCGGA TCTGTGGGGG CGGGCCCCCC CTTTCCCCCC C TCAGTGACA     1800
CAGGCTGCAA GGAATGTCTG GGCCTCAATG GACCTTGTGT AAGATGAGGG G TGGGGGGCA     1860
GAGCAAGTAC ACACCTTAAG GCAGGGCCAG AACAAGAGGG AGCTCCTGGA C TGGGCTGCA     1920
CACATTCCCA GGGCTCCTCC CGGCACTGCG GCCTCAGTCT GTGCCCACGC T TGGTCTATG     1980
GACCTGGGCG CCTGCACAGT TCACACACGG ACATAGTTGG CCTTCACCTT T CAGTTTCCA     2040
AGGAGTCTTC AAAGAACTCA TGAAGAGTTC CAGACTCAGA GAGCTTATCC T AGAAGACAG     2100
ACAGACAGAC AGGAAGACCC TGAGGAGGTC TGCTCTTATT TAATTCTGGA G ACCCAGCTG     2160
AGGGGCACCG TGGAGCTGCT CCCTGTCCCC TCCCAGCCTG GCCCCTTGA T GCCACTGGA      2220
TGATGCAAAA AAAAGTACTA ATGGAGGCCT GCCCCTGCCC CAGCTGTTGG C TCCATTCCT     2280
ACGTCACGCC GAGGTAGGCT CGGCCTTCTC ACACCTTTTG CACCTGCCTA G TGTAGCTTC     2340
ACCACATTTC CGCACTTAGT AGGTCCCTGG GGCCTTGGGT GTTTCAGCCT T ACATCCTGT     2400
GAGACCTTGA GCCTCTCCCA TCTCCCCTCA CAAGGCTGCC TTACTCCTAC G CACACGGGC     2460
AGAGTAGGCA GGTGCAGCTC TGACAAGTCC AGAAGCAGCA GTCTCAACCT G TGTGCTGGG     2520
ACCCCTTTGA GGGTCGAGCA GTCCTTCACA GGGGTCACAC TTGAGATATT T ATCTTCTTC     2580
TTCTTCTTCT TTTTGTTTTT CAAGACAGGG TTTCTCTGTG TAGCCCTGGC T ATCCTGGAA     2640
```

```
CTCACTCTGT AGACCAGGCT GGCCTTGAAC TCGAAATCTG CCTGCCTCTG A TTCCCCAGT   2700

GCTAGGATTA AAGGAGTGTG CCAACACTGC CCGGCTCATG TTATGATCTT A AGGGCAGCA   2760

AAATTACAGT GGTGAAGTAG CAATGAAAAT AATTTTCTGG CTGTGAGGTC A CCACCGCAT   2820

TAGGGAAACT GTATTAAAGC GTCACAGAGT TAAGAAGGTT GAGAACTACT G CCTTCGAGA   2880

TTCAGAGACA AGGTTCAAAT TCTAGTTTGA ACATGGAACT AATTCAGGCA A GCTCATCTT   2940

CTTAACTGGG CCTCACTGTG ACCTGTCTCA CTGGGTTCAG ACCTCCCTGT C CATGCATGT   3000

GAGGCCAGGT AAACAGACAT CCACAGGGTC CTGATTGGGA TTAGCCTCTC T CACCCCTGG   3060

GAGTGGGCAT CGTGACCTGC AAGAGATTAG TATTAGTCTT GTCCTTTAGA C TTAGGTGTC   3120

TTGGGTCCCA TGACTGAGCT GTTGTGACCC TAGCACCTTC CTCAGGATAT A GGAGCCAAG   3180

CAGGGGGCTG GGCTGAGTTG GGCCACTTTC CTGTGTTATA GGAAGTCCTC T CACCACTGC   3240

TTCTGTCCTG CATGCAGCTG CCCCAGGAGC TCCTGTGTCC TTGAGGTATT G AGACTGCGG   3300

GAATTGAGGG CACTGAGTCT AGGCCTTGGG TGCTCAGTCT CTTTGGGGAC T CTGGAGGAA   3360

GTGGGAGGTA CCAGGGAGGA AGGTCTCTGG GGACGGACGT CTCCCTTTGT A CAAGTGGGC   3420

AAGACTCAGA CACCAGTGAC TGCTTTGATT TCCGTTCTGG TGAAAACTGT T CAGAATTTG   3480

GTGGCAACCC TCACTTTGAG CCTAGTTCCA CAGCCAAGGT GTACAGGGGA G AACTGGGAG   3540

GGGCCGGTGC CACTAGACCC AGTCACTAGC ACCCCGAGAG CAAAGCATCC C AGTTCAGCT   3600

CCCAGCCTTG ACCTAAGCCT GGGATGGGGC TGGAAACTTC AGCCCAGGCA G ACAAGGAAG   3660

TGGCCAGGAA AGCGGAAGCA GCTTTGATGG TCCGGAGGGG GCCGGAAGCT A AATGGGGTG   3720

GTGGAAGACT GGGCTGGGGG CCTGAGTTCC TGTTTTCTCC CCAGGCCCAT C TGAACAGCC   3780

CCCTCCTCTG CAGTGCAGGA ACCTCTGAAC GCTCAGCCTT CTGGCTGGGC A CCAAGGACC   3840

CGTGCCCACC AATGCGGCCC GGCCCCCAGA GAGTCAGGCC CACAGGAGCA C GCCCATGTG   3900

GGCCGGCGGT GTGGGAGCC CTCGGCGGGT GCATGGCCTG CACCTACCGA T GACCTCTTT   3960

GCCCGTAGCT TCGCCAACCT GCCCGGCCCC CACTGACACC ACATACCTTT G AGCCGAGGC   4020

CAGCTCGGGC CACTCTTGCG CAGTGGCAGT GATGCTGGTG AAGTCGGCCC C CTACACCAG   4080

CCAGCCCCCG TGCCCGTGCC CACAGCCACG AGGATGCCAG CCGCCCTGCT G CAACCCCTA   4140

CTCGGCTCTT CACTGACCCA CTGGCACTGC TAGGGTTGCC AGCAGAAGAG C CAGAGCCCA   4200

GGTTCCCGCC AGTGCTGGAA CCCCGGTGGT TTGCTCACTA TGATGTGCAG A GCTTGCTCT   4260

TTGACTGGGC TCCACGACCT CGGGGACAG GCAGCCATAC AGAGGCAAAC T CTGGGACCT   4320

TAGCTGAGGG CCAGACTACC ACCTCAGATC TACTGCTCGG GGCACCTGGC T TTGTGAGCG   4380

AGCTTGGTGG TGAGGGTGAG CTAGGGCTGG GTGGGCCAAT ATCCCCACCT G TGCCCCCTG   4440

CACTGCCTAA TGCGGCTGTG TCCGTCCTGG AGGAGCCACA GACCCGGACC A CACTTACAG   4500

CCTGGAGCAC GCAGATCTGG GTGCAGGCTA CTACCGCAAG TACTTCTATG G CAAAGGTAA   4560

GGGGCAGGCG AGCCTGGGAG AGGCAGGAGA GGATCTGGGT CGGAGGTCCC T GTGGTCTTC   4620

TACATTCTAT CAGTGGGAGG CTCATGGGCT GGCCTTCCCT GTAAAAAAGG G GCAGGAGCT   4680

GAATTGGGCT CTGTTGGCTC AACTCTGACC ACCTCTTTAA GGCCAAGAAT G GTGTCACAC   4740

CTGAAGTCAG GGAGTGCACT TACCTCTGAG GCTCATCTTC ATAACCTCCA G GAGGCCAGT   4800

GAGCGATTTC CTATTTCCAT ATCTGTGTGA TGAAACCCTG TTCTCATCAT T AGCAGGAAA   4860

AGCAGCTTCC GTGTCTTGAA TGGGAGAACC TAAGCTTTGG TGGAGCCAGG G CAGCATTTA   4920

ACTAGGAGGA CTTAGGCATT TGTTCCCCGG TCCTGGGAAC AAGGTGTAAC C GTGGGTGGG   4980
```

| | | | |
|---|---|---|---|
| ACTGCAAACT GGGGTGGAGT GAACTCCCAG GTTCAGCGCT TGGTGAGAGA A TACCTAGGG | 5040 |
| TGGTACTTCT GTGGTGGGAG TAGTCAAGAA GGGATAGGGT GGTCTGTGGG T TTGACTGAA | 5100 |
| AGGCCACCGA CCGACCAACC AACGACCCTC CACCCCCACC CCCACAGAAC A CCAGAACTT | 5160 |
| CTTTGGGTTG GATGAGGCGC TGGGTCCGGT GGCCGTGAGC CTGCGACGGG A GGAGAAAGA | 5220 |
| GGGCAGCGGA GGGGGCACCT ACACAGCTAC CGGGTCATCG TGCGGACCAC G CAGGTGGGC | 5280 |
| TGGGATTACA GGCTCAGGAG GCAGGTTTCC TCCACCACAG CCTATACAAA A ACTGAATGT | 5340 |
| CTCTACATCC TTAGCTCCGG ACCCTCCGTG GCACCATCTC GGAGGACGCA C TGCCTCCCG | 5400 |
| GCCCCCCGAG CGTATCTCCG AGGAAGCTTC TGGAACATGT GCTCCACGGC T GAGCCCACC | 5460 |
| TGCCTGCGCC TGGGTTCAGC CTCTCCCAAG GTGCCCCGCA GCTGCTTACT C TGGATGAGC | 5520 |
| AAGTGGTGAG TGGCTGGGAG GTAAGGAGGG AGTGCAGCAT CCCGGGGAAG A TGGGGCTGA | 5580 |
| CCTTCATCTC CCTAACTAGC TAGCTTCCCG CTCCCTAACC CTGACCTGAT C TGACGGACC | 5640 |
| TCAAGGTACA GCTGATCCAC CTCCAAGCCT TTCCGAGAGA AGGATCC | 5687 |

(2) INFORMATION FOR SEQ ID NO: 4:

(i) SEQUENCE CHARACTERISTICS:
        (A) LENGTH: 6645 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(904..1 015, 1356..1459, 1726..1883, 2009
           ..2618, 2890..3164, 4291..4509, 4598..4709, 4795
           ..4903, 5017..5117, 5200..5255, 5447..5525, 5598
           ..5741)

(xi) SEQUENCE DESCRIPTION: SEQ ID NO: 4:

| | | |
|---|---|---|
| GGATCCCCAT TACAGATGGA TGTGAGCCAC CATGTGTTGC TGGGAATTGA A CTCAGGAAC | 60 |
| CTCTGGAAGA GCAGTCAATG CTCTTAACCA CTGAGCCATC TCTCCAGCTA A CCTTGTTTC | 120 |
| AAACAAACAA AAAATTGCAG GTACGTGTCT AGATTCCAAT ATTTGGGAGA T ACAGGCAAA | 180 |
| TGATCAGGAT CAGGCAGTCT TAGCTATATA TGAGTTTAAG TACAGCCTGG C CTATGTACT | 240 |
| ATAGCCTATC AAAAGACAA ACAGGAAGGG GACAGAAATG ACTCCAAACC T CAGAGGGCT | 300 |
| GGGGTGCCAG CACACTGGAG CCTTGAGCTG AGGGGGACGG GAACATGGGC A CCAGTCTTG | 360 |
| GCAGGGGATC TCAGCCTTCC TAGTGCCCTT TCCCACAGCT CCACATGGTG T GGTGACCCT | 420 |
| GATCAAAAAT TATTTTCATT GCCACTTCAT AACTGTAATT CTGCTACCCT T AGGAATTGT | 480 |
| ACCATAAACA CCTGACACAC AGGGTCTCTG CTGCATGCGA CCCCTGTGAA T GGGCCGTTA | 540 |
| GACCCTCAGA AGGGTCACAA CTATAGGCTG AGAACCCACT GGTGTATAGG G TCCTTTCTG | 600 |
| GGAGTTATCT CTTTTGTTGC TGGAGAAGTC ATTAAATCCT CTGCCTCTTC C CTGTGACCT | 660 |
| CCCTGCTCTC ACGAGCACAG GAGAGGGCAG GTAGAACGCA CTTGATGGGC A AAGATGCCC | 720 |
| AAATGGCTCA GAGTTCCTAC CAGGGCAGCC CAGCCCCAAA GGCCAGCTCT T CCCATTCTG | 780 |
| TACAGGGTGG GCTGCCAGGG TACTGAAGCC TTTGTCTTCT GTTGTCCATG A CCCCCTCAG | 840 |
| CTGAGCTTCC AACGCAAGGT GGGCATCCTG TACTGCCGCG CAGGCCAGGG C TCTGAGGAA | 900 |
| GAG ATG TAC AAC AAC CAG GAG GCC GGA GCA G CC TTT ATG CAG TTC CTT | 948 |
|     Met Tyr Asn Asn Gln Glu Ala Gly Ala Ala Phe Met Gln Phe Leu | |
|      1             5             10            15 | |
| ACT TTG CTG GGT GAT GTG GTG CGA CTC AAA G GC TTT GAA AGT TAC CGG | 996 |

```
Thr Leu Leu Gly Asp Val Val Arg Leu Lys Gly Phe Glu Ser Tyr Arg
            20                  25                  30

GCC CAG CTG GAT ACC AAA A GTGAGCGTCC CCCGCCCCTA  AGGGACTGGA        1045
Ala Gln Leu Asp Thr Lys
                35

GATGCAGGGC AGAACTTTAT CAGTGTTCCT TAGTCTGTGG TGGCTGGGGC T GAGAATGGG  1105

GGAGTGCCCT GCTCCCTCTA AGTCTTATTT CTGGATTCGT TCTATCTCAG C ACCCCTATA  1165

CTGATTCCCC TTCACCCTGG TGTGGGGCCG TAGTCTATAG GAGAGGGGAG G GAATTTACC  1225

AAGGATGGGG CTCTTGGTCT TCGTGGCCTA AGCAATAGCT GGTGGCTGGG A CATAGAAGT  1285

AAATTTAAGA CTCATTGAAG TCACCCACAC CCCCCATGTT CTCTTTGTGT C CCCAATTGT  1345

CTGGCTACAG  CG GAT TCC ACG GGC ACA CAC TCA CTC TAC ACC ACC TAC      1393
            Thr Asp Ser Thr Gly Thr His Ser Leu Tyr Thr Thr Tyr
                 40                  45                  50

CAA GAC CAT GAG ATC ATG TTT CAC GTG TCC A CG ATG CTG CCT TAC ACG   1441
Gln Asp His Glu Ile Met Phe His Val Ser T hr Met Leu Pro Tyr Thr
                55                  60                  65

CCT AAT AAC CAG CAA CAG GTGTGTGAGG AGCTGGGCCA G GCCAAAGAC           1489
Pro Asn Asn Gln Gln Gln
                70

TTTCGGGAAG CAGTGGCGGG TGTTACTTGA GTGCTTAATA TCAGAACGGT G GTCTGAGCT  1549

CTGCTGAACC TAACAACACC CACCCCCCCA CCCCTTGGCT GTACCACCTT C GCAAATACC  1609

CTCCTCGGGC CTTTATAAGG TGCAGGTGGG GAACCACTGA CACCTTTGCC A TGCCTAAAT  1669

GAGGGACTGG GGGGGGCACA AAGCTCACCT CTCATTTGCC TACCTTTAAC C CCCAG      1725

CTC CTG AGG AAG CGT CAT ATC GGC AAC GAT A TT GTG ACC ATC GTG TTC   1773
Leu Leu Arg Lys Arg His Ile Gly Asn Asp I le Val Thr Ile Val Phe
            75                  80                  85

CAG GAG CCC GGT AGC AAG CCC TTC TGC CCT A CA ACA ATC CGC TCT CAC   1821
Gln Glu Pro Gly Ser Lys Pro Phe Cys Pro T hr Thr Ile Arg Ser His
            90                  95                  100

TTC CAG CAC GTT TTC TTG GTG GTG CGT GCG C AT GCT CCC TGC ACC CCA   1869
Phe Gln His Val Phe Leu Val Val Arg Ala H is Ala Pro Cys Thr Pro
105                 110                 115                 120

CAC ACC TCA TAC AG  GTGGGTGCTA GGGTGAACTC AGGTC ATGGG CACCGATGAT    1923
His Thr Ser Tyr Arg
                125

TGACACATTC CTCGCACCGA TGATTGGACA CATTCCTCGC CCCCTTCCGC C CCACGTTCC  1983

CTCACTACAG CCTTCCTCCA CGCAG G GTG GCA GTG AGC C GC ACC CAG GAC      2033
                          Val Ala Val Se r Arg Thr Gln Asp
                                         130

ACT CCT GCC TTC GGG CCT GCG CTG CCA GAA G GC GGA GGC CCC TTT GCA   2081
Thr Pro Ala Phe Gly Pro Ala Leu Pro Glu G ly Gly Gly Pro Phe Ala
135                 140                 145

GCC AAT GCC GAT TTC CGG GCC TTT CTG TTG G CT AAG GCA CTC AAT GGT   2129
Ala Asn Ala Asp Phe Arg Ala Phe Leu Leu A la Lys Ala Leu Asn Gly
150                 155                 160                 165

GAG CAA GCG GCT GGT CAT GCA CGC CAG TTC C AC GCC ATG GCT ACA CGC   2177
Glu Gln Ala Ala Gly His Ala Arg Gln Phe H is Ala Met Ala Thr Arg
                170                 175                 180

ACA CGC CAA CAG TAC CTG CAG GAC CTG GCT A CT AAT GAA GTG ACC ACT   2225
Thr Arg Gln Gln Tyr Leu Gln Asp Leu Ala T hr Asn Glu Val Thr Thr
                185                 190                 195

ACT TCG CTG GAC TCG GCT TCG CGG TTT GGC C TG CCA TCT CTG GGG GGT   2273
Thr Ser Leu Asp Ser Ala Ser Arg Phe Gly L eu Pro Ser Leu Gly Gly
            200                 205                 210
```

```
AGG CGC CGG GCA ACC CCT CGG AGC CCA GGC G CG GAC GTA CAG GCG GCG        2321
Arg Arg Arg Ala Thr Pro Arg Ser Pro Gly A la Asp Val Gln Ala Ala
    215                 220                 225

GGT GCG CTG ATG TGG GGC GTA CGC GCG GCT C CA GGG GCG CGG GTC GCA        2369
Gly Ala Leu Met Trp Gly Val Arg Ala Ala P ro Gly Ala Arg Val Ala
230                 235                 240                 245

GCG GGA GCT GAA ACG AGC GGT CCG GAC GAC G CC GAG GTG CCC TGC TTG        2417
Ala Gly Ala Glu Thr Ser Gly Pro Asp Asp A la Glu Val Pro Cys Leu
                250                 255                 260

TTG GGC ATC TCA GCA GAG ACA CTG GTG CTG G TG GCA CCT CGC GAC GGC        2465
Leu Gly Ile Ser Ala Glu Thr Leu Val Leu V al Ala Pro Arg Asp Gly
            265                 270                 275

CGC GTG GTC TTC AAT TGT GCC TGT CGC GAC G TA TTG GCC TGG ACC TTC        2513
Arg Val Val Phe Asn Cys Ala Cys Arg Asp V al Leu Ala Trp Thr Phe
        280                 285                 290

TCA GAG CAC CAA CTC GAT CTG TAC CAC GGG C GC GGG GAG GCG ATC ACG        2561
Ser Glu His Gln Leu Asp Leu Tyr His Gly A rg Gly Glu Ala Ile Thr
    295                 300                 305

CTG CGG CTC GAC GGG GCC CCA GGG CAA GCC G TG GGC GAA GTC GTG GCA        2609
Leu Arg Leu Asp Gly Ala Pro Gly Gln Ala V al Gly Glu Val Val Ala
310                 315                 320                 325

CGT CTG CAG GTGAGGCAGT GTCAAAAACT AAGGTCCCCT GGTCGGGT GC               2658
Arg Leu Gln
GTATCGGGGG CGGGGCCTAT TGGAAACTCC GTTAGCTGCT GTGGTGGGGC G GGGAAAAGG     2718

TACTTGCACA GGTGACTCTC AGAGTCTCCA ATTCGAATAC ACAACTATCA G GTAGGTCGC     2778

TAGGGCTCCT GGGGCATGCC GGGTTAAATC GATCGAGGCA GGGGCGGGAC C AGGGCGGGG     2838

CCTCTGTGAA GCCACGCCCC AAGGCCACTC TCACCCAGCC TTTCCTTGCA G    CTG GTG    2895
                                                            Leu Val
                                                            330

AGC CGC GGG TGT GAG ACC AGA GAA CTA GCG C TG CCC AGA GAT GGC CAA        2943
Ser Arg Gly Cys Glu Thr Arg Glu Leu Ala L eu Pro Arg Asp Gly Gln
                335                 340                 345

GGT CGC CTG GGC TTC GAG GTG GAT GCA GAA G GC TTC ATC ACG CAC GTG        2991
Gly Arg Leu Gly Phe Glu Val Asp Ala Glu G ly Phe Ile Thr His Val
            350                 355                 360

GAG CGC TTC ACG TTT GCG GAG ACC ACG GGG C TT CGG CCT GGA GCT CGT        3039
Glu Arg Phe Thr Phe Ala Glu Thr Thr Gly L eu Arg Pro Gly Ala Arg
        365                 370                 375

TTG CTG CGA GTC TGC GGC CAG ACG CTG CCC A AG CTG GGT CCC GAA GCT        3087
Leu Leu Arg Val Cys Gly Gln Thr Leu Pro L ys Leu Gly Pro Glu Ala
    380                 385                 390

GCT GCC CAG ATG CTG CGC TCT GCG CCG AAG G TC TGC GTC ACG GTC CTA        3135
Ala Ala Gln Met Leu Arg Ser Ala Pro Lys V al Cys Val Thr Val Leu
395                 400                 405                 410

CCC CCA GAC GAG AGC GGC CGG CCG CAG AG   GTCAGGGCAC CGGGTGGGGG         3184
Pro Pro Asp Glu Ser Gly Arg Pro Gln Arg
                415                 420

TTGTGGGGGG TGGGTAGGAG GACTCAGCGG CTGGCCCATT CTGTGCCTCC C GTGTTAGCA     3244

TCAGCATGCT CTGAATCGTA CGGTATTCAT CTAGACTTGA AACTGTTTAA G CTCGTGCTT     3304

TCCCTCTCTA AAGGTTAAAT AGCTCCTTCT ATTATTTCAA TGTATTAGCT C CTCCACACC     3364

AAGTACACAC TAATTGACCA CTTCCTATTC TAAACCCAAT ATAGGCAAAC T TTCCCCATA     3424

GAACCCCTAA TAGTAAATAC TTTTAGACTT TTGGAGCCAC TATTCTTGCC A CAGTCACTC     3484

GACTCTTTTG TAGGAAAATG AATGTGTGCC AGCATCTACT AAAACTATGA C TGGAATTTT     3544

AGGATTTGAT TTGGAGCTCC TTGTCTTGTG AAGGGGTAAA CCCAATGTAA G GTCAAAAAA     3604

AAAAAAAAAT CCAAGTAGAA ACACATTATG CTCAGACTGT GTAATTTTTA C ATGCCATGA     3664
```

```
AGTACTCTAT TAATACCTTT TAAATTATTT AAACATCTAA GAACTAAGGC C AGAGAAGTG       3724

GCTCAGCCAT TAAGAGCATT TGCTGCTCTT GCAGAGGACC TGAGTTGGAT T CCTAGCACC       3784

CACACAGTGC TCTGTGACAG CCTGTATGTA ACTTCAGATC CAGGGGTCTC A CACCCTCTT       3844

CTGGTCTCCA CAGGTGTTGC ATTCACATGT GCCTGCTCCC TCCCCACGTA A ATACACATA       3904

TACACATCAA TAAATAGTTC AAGATCTCTA AAAACTATTC TTAGCAGATA G GAGTTTCAA       3964

AGACTGGCAT GTGTGCTAAT AAAAAACAAA GAGAAGCATG GGCTGGATGG C TCCAGGCAG       4024

TGCACTGTGG ATGCTAAGCG ATTTATATTA CATTGTTTCC ACTGTAAATA C TCTTATGTA       4084

TGTTTGACAG AAAACAGAGA GAGTGGCCTG CTTAGGAGAC ATGGGCAGCC A TGGATACAA       4144

AGTTAACAGT GATATTTGTC TGCTGTAGAG TCAGGATGCC TGGAGCTCTC T TCCTTTTGG       4204

ATGTCTCTGG CAGTGGCTGG GATGGGGTGG ATGCTGTGGA GGGGATGGAG G GTCCTACCT       4264
```

```
GATGCTGCCC CACCCCACCC CTCCAG G AGC TTT TCG GAG CTC TAT ATG CTC                4315
                              Ser Phe Ser Glu Leu Tyr Met Leu
                                                     425

TCT CTG AAG GAA CCC AGC CGG CGG GGG GGC C CA GAG CCA GTA CAG GAT             4363
Ser Leu Lys Glu Pro Ser Arg Arg Gly Gly P ro Glu Pro Val Gln Asp
     430                 435                  440

GAA ACT GGG AAG TTG GTC ATA TTG CCT CCC A CC AAG CAG CTG CTA CAT             4411
Glu Thr Gly Lys Leu Val Ile Leu Pro Pro T hr Lys Gln Leu Leu His
445                 450                 455                 460

TTT TGC CTG AAA GAC AGC AGC AGT CCT CCG G GG CCT GGG GAT CTG ACT             4459
Phe Cys Leu Lys Asp Ser Ser Ser Pro Pro G ly Pro Gly Asp Leu Thr
                465                 470                 475

GAG GAG AGG ACA GAG TTC CTG CGC AGC CAC A AC TCC CTG TCA TCT GGA AG          4509
Glu Glu Arg Thr Glu Phe Leu Arg Ser His A sn Ser Leu Ser Ser Gly Ser
480                 485                  490

GTACACTCAC TGGGCCAGCC TTTTAGGACC TGAAAGCACA GCTCTGGAAA A GCAGCTCTC          4569

CGTTCTGAGT CACCCCTACC CTCCTTAG C TCC CTG TCC GAT GAG GCT CCA GTC             4622
                                 Ser Leu Ser Asp Glu Ala Pro Val
                                      495                 500

CTG CCC AAC ACC ACT CCA GAC CTC CTC CTT G TC ACC ACT GCC AAC CCA             4670
Leu Pro Asn Thr Thr Pro Asp Leu Leu Leu V al Thr Thr Ala Asn Pro
         505                 510                 515

TCT GCA CCT GGT ACT GAC AGA GAA ACA CCC C CT TCC CAG GTAAGCAGAA              4719
Ser Ala Pro Gly Thr Asp Arg Glu Thr Pro P ro Ser Gln
     520                 525                 530

ACAAACAGAG CTCTGGAGAT TCATTGCAGA GGTGACATTG GATGCTACAG C CTTGCTGTT          4779

CACTTTTGTC CCCAG GAC CAG TCA GGA AGC CCC AGT AGC CAT GAA GAC ACC            4830
              Asp Gln Ser Gly Ser Pro Ser Ser His Glu Asp Thr
                                  535                 540

AGT GAC TCA GGC CCA GAA CTG AGG GCC TCC A TC CTG CCC AGA ACC TTG             4878
Ser Asp Ser Gly Pro Glu Leu Arg Ala Ser I le Leu Pro Arg Thr Leu
545                 550                 555

TCT CTG CGG AAT TCC ATC AGT AAG A GTGAGTCTGG  AGCCAGGGAA                     4923
Ser Leu Arg Asn Ser Ile Ser Lys
560                 565

TAGGGCAGGA GGAGAAGACA GCCCCTCCCC CCCATTCCAG CCCCTCCCTC C CCCCAGCCCC         4983

CACCCTCCCT AAGCCTTCTC CTTTGACCTG CAG TT ATG TCG GAA GCT GGC AGT             5036
                                       Ile Met Ser Glu Ala Gly Ser
                                                          570

GAG ACC CTG GAG GAT GAG TGG CAG TCC ATC T CA GAG ATC GCC TCC ACT             5084
Glu Thr Leu Glu Asp Glu Trp Gln Ser Ile S er Glu Ile Ala Ser Thr
575                 580                 585
```

```
TGC AAC ACA ATT CTG GAG TCA CTG TCC CGG G AG GTGAGGCCGC AAGGCCCAGA     5137
Cys Asn Thr Ile Leu Glu Ser Leu Ser Arg G lu
590                 595                 600

GGGAGGAGCC AGGAGGATGT TTATCCCTTC AGACCTGCCC ACAGTCTCTC T CTCTCCTAT     5197

AG GGA CAA CCC ATC TCA GAG AGC GGA GAC CC C AAG GAA GCT TTA AAG        5244
   Gly Gln Pro Ile Ser Glu Ser Gly Asp  Pro Lys Glu Ala Leu Lys
                 605                 610                 615

TGT GAT TCT GA  GTAAGTTTTC TGCCCTCACA TACCCACTCT TGTGTGTGTG            5295
Cys Asp Ser Glu

TCCTTCCCTG CCTGCCCATT GCAGTTGAAC ACTATCTAGG CTCTGCATCC A CAGATACCT     5355

AAGTCTCAGA AGACAGGGTT GGGTTCATTA TCAGTCAGGA GTGTCTGGGA G CCTGCACTG     5415

CTTCCGCTGA GTTCTGACCC CATGTCCTCA G G CCA GAA CCC GGG AGC CTG TCA      5468
                                   Pro Glu Pro Gly Ser Leu Ser
                                                    620             625

GAA AAG GTC TCT CAC CTA GAG TCC ATG CTC T GG AAG CTC CAG GAG GAC      5516
Glu Lys Val Ser His Leu Glu Ser Met Leu T rp Lys Leu Gln Glu Asp
                630                 635                 640

CTG CAG AGG GTGAGGAGAG AGCCTGACGG GGGCGCACAG GGCTGCCC CT              5565
Leu Gln Arg
       645

GGCAAGGCTC TGACTACCAT TCTTCAACCT AG GAG AAG GCG GA C AGG GCA GCC      5618
                                    Glu Lys Ala Asp Arg Ala Ala
                                                        650

TTG GAG GAG GAG GTT CGG AGC CTC AGA CAC A AC AAC CAG AGG CTG CTG      5666
Leu Glu Glu Glu Val Arg Ser Leu Arg His A sn Asn Gln Arg Leu Leu
                655                 660                 665

GCA GAG TCC GAG AGT GCC GCC ACC CGC CTG C TC CTG GCC TCT AAG CAT      5714
Ala Glu Ser Glu Ser Ala Ala Thr Arg Leu L eu Leu Ala Ser Lys His
                670                 675                 680

CTG GGT GCA CCC ACT ACT GAC CTG GCC TGAGTTCC AA TCTGAATCTG            5761
Leu Gly Ala Pro Thr Thr Asp Leu Ala
685                 690

GACCTGCTTG GAACTGCCTG GCCCCTCAGA GCAACTGGGT CATACTAGTG C CCTTCCTCA     5821

GGACTTCTTC CCTGCGCTGA GGCGCGTCTT AGCACTGCCC CCTCTTCCCA G CCCATTTGG     5881

TGGCTAATGC CTGTCCCTGT TTGTAAATAT CCTGTAAAGA AAAGGAGACA T CAGAGTTTA     5941

AAAAAAAGAA ACAACAAGAA GAAGCAAACA ACTCTATTTG TGTTTGTGTG T CAAGATACA     6001

GAGGAGGGGG AGTCATCCCC TTTCCAAGGT CATATCAAGC TCCTAGGAGC A GTAGGACAG     6061

GTCCCAGGGG GGACATTGAC TTAGTGTTAA TCTGGCACCA AGCAGAGGCT C TGAGGATAG     6121

AACACCCCCT TGGCTCCCCT TCATTTATTG GGTTCTCTTG GAAAGCAGGT G CCACGCTT      6181

CATGCCTGTC TGTTTGGAGC AGGAGAGGGA ACACTTCGAG CCTGCAGAGC G AACAACCAG     6241

GGGTGGGCTC TGGCCATGCA GTATGGAATT CCCGAATAGG CCCTGCTAAG C TGAGCTTCA     6301

GAGCATCATT GACTACCACT GGATGGATCA CCTGTTGCAG GCCCCAGCCA G TGCCTCATC     6361

AGCCTCTCCC CAGGGCTGCC TCTGCCTCGA GAAGCCCAGA CCCTGAGAGA G GACAGGATA     6421

AACATGGCTG AGTAACAGTG GGGCCATGAG CACAAGGAAG CCTTCTCTGA G GAGGCTAAT     6481

AAAAGGACTG AGTTTTGAAA GTTGAGTTCA CCAGCAGATG TCACAGGTAT C CAGGAGAAA    6541

CACTCTAGGA GCCACTGGGC CGAATTTGAG GTACCGAAGG AATCAGGGTT A CAGAGCCTT    6601

TAAGCTGGGT CAGAAAGGGT CATGCCAAGG TCCACTAGGG ATCC                     664 5
```

(2) INFORMATION FOR SEQ ID NO: 5:

(i) SEQUENCE CHARACTERISTICS:

(A) LENGTH: 693 amino acids
      (B) TYPE: amino acid
      (D) TOPOLOGY: linear (ii) MOLECULE TYPE: protein (xi) SEQUENCE DESCRIPTION: SEQ ID NO: 5:

Met Tyr Asn Asn Gln Glu Ala Gly Ala Ala Phe Met Gln Phe Leu Thr
 1               5                  10                  15

Leu Leu Gly Asp Val Val Arg Leu Lys Gly Phe Glu Ser Tyr Arg Ala
             20                  25                  30

Gln Leu Asp Thr Lys Thr Asp Ser Thr Gly Thr His Ser Leu Tyr Thr
         35                  40                  45

Thr Tyr Gln Asp His Glu Ile Met Phe His Val Ser Thr Met Leu Pro
     50                  55                  60

Tyr Thr Pro Asn Asn Gln Gln Gln Leu Leu Arg Lys Arg His Ile Gly
 65                  70                  75                  80

Asn Asp Ile Val Thr Ile Val Phe Gln Glu Pro Gly Ser Lys Pro Phe
             85                  90                  95

Cys Pro Thr Thr Ile Arg Ser His Phe Gln His Val Phe Leu Val Val
            100                 105                 110

Arg Ala His Ala Pro Cys Thr Pro His Thr Ser Tyr Arg Val Ala Val
            115                 120                 125

Ser Arg Thr Gln Asp Thr Pro Ala Phe Gly Pro Ala Leu Pro Glu Gly
130                 135                 140

Gly Gly Pro Phe Ala Ala Asn Ala Asp Phe Arg Ala Phe Leu Leu Ala
145                 150                 155                 160

Lys Ala Leu Asn Gly Glu Gln Ala Ala Gly His Ala Arg Gln Phe His
                165                 170                 175

Ala Met Ala Thr Arg Thr Arg Gln Gln Tyr Leu Gln Asp Leu Ala Thr
            180                 185                 190

Asn Glu Val Thr Thr Thr Ser Leu Asp Ser Ala Ser Arg Phe Gly Leu
            195                 200                 205

Pro Ser Leu Gly Gly Arg Arg Arg Ala Thr Pro Arg Ser Pro Gly Ala
            210                 215                 220

Asp Val Gln Ala Ala Gly Ala Leu Met Trp Gly Val Arg Ala Ala Pro
225                 230                 235                 240

Gly Ala Arg Val Ala Ala Gly Ala Glu Thr Ser Gly Pro Asp Asp Ala
                245                 250                 255

Glu Val Pro Cys Leu Leu Gly Ile Ser Ala Glu Thr Leu Val Leu Val
            260                 265                 270

Ala Pro Arg Asp Gly Arg Val Val Phe Asn Cys Ala Cys Arg Asp Val
            275                 280                 285

Leu Ala Trp Thr Phe Ser Glu His Gln Leu Asp Leu Tyr His Gly Arg
        290                 295                 300

Gly Glu Ala Ile Thr Leu Arg Leu Asp Gly Ala Pro Gly Gln Ala Val
305                 310                 315                 320

Gly Glu Val Val Ala Arg Leu Gln Leu Val Ser Arg Gly Cys Glu Thr
                325                 330                 335

Arg Glu Leu Ala Leu Pro Arg Asp Gly Gln Gly Arg Leu Gly Phe Glu
            340                 345                 350

Val Asp Ala Glu Gly Phe Ile Thr His Val Glu Arg Phe Thr Phe Ala
        355                 360                 365

Glu Thr Thr Gly Leu Arg Pro Gly Ala Arg Leu Leu Arg Val Cys Gly
        370                 375                 380

-continued

```
Gln Thr Leu Pro Lys Leu Gly Pro Glu Ala Ala Gln Met Leu Arg
385                 390                 395                 400

Ser Ala Pro Lys Val Cys Val Thr Val Leu Pro Pro Asp Glu Ser Gly
                405                 410                 415

Arg Pro Gln Arg Ser Phe Ser Glu Leu Tyr Met Leu Ser Leu Lys Glu
            420                 425                 430

Pro Ser Arg Arg Gly Gly Pro Glu Pro Val Gln Asp Glu Thr Gly Lys
            435                 440                 445

Leu Val Ile Leu Pro Pro Thr Lys Gln Leu Leu His Phe Cys Leu Lys
        450                 455                 460

Asp Ser Ser Pro Pro Gly Pro Gly Asp Leu Thr Glu Glu Arg Thr
465                 470                 475                 480

Glu Phe Leu Arg Ser His Asn Ser Leu Ser Ser Gly Ser Ser Leu Ser
                485                 490                 495

Asp Glu Ala Pro Val Leu Pro Asn Thr Thr Pro Asp Leu Leu Leu Val
                500                 505                 510

Thr Thr Ala Asn Pro Ser Ala Pro Gly Thr Asp Arg Glu Thr Pro Pro
            515                 520                 525

Ser Gln Asp Gln Ser Gly Ser Pro Ser Ser His Glu Asp Thr Ser Asp
530                 535                 540

Ser Gly Pro Glu Leu Arg Ala Ser Ile Leu Pro Arg Thr Leu Ser Leu
545                 550                 555                 560

Arg Asn Ser Ile Ser Lys Ile Met Ser Glu Ala Gly Ser Glu Thr Leu
                565                 570                 575

Glu Asp Glu Trp Gln Ser Ile Ser Glu Ile Ala Ser Thr Cys Asn Thr
            580                 585                 590

Ile Leu Glu Ser Leu Ser Arg Glu Gly Gln Pro Ile Ser Glu Ser Gly
            595                 600                 605

Asp Pro Lys Glu Ala Leu Lys Cys Asp Ser Glu Pro Glu Pro Gly Ser
        610                 615                 620

Leu Ser Glu Lys Val Ser His Leu Glu Ser Met Leu Trp Lys Leu Gln
625                 630                 635                 640

Glu Asp Leu Gln Arg Glu Lys Ala Asp Arg Ala Ala Leu Glu Glu Glu
                645                 650                 655

Val Arg Ser Leu Arg His Asn Asn Gln Arg Leu Leu Ala Glu Ser Glu
            660                 665                 670

Ser Ala Ala Thr Arg Leu Leu Leu Ala Ser Lys His Leu Gly Ala Pro
        675                 680                 685

Thr Thr Asp Leu Ala
    690
```

(2) INFORMATION FOR SEQ ID NO: 6:

(i) SEQUENCE CHARACTERISTICS:
        (A) LENGTH: 240 amino acids
        (B) TYPE: amino acid
        (C) STRANDEDNESS: single
        (D) TOPOLOGY: linear (xi) SEQUENCE DESCRIPTION: SEQ ID NO: 6:

```
Gly Gln Gly Ser Arg Arg Arg Asn Tyr Asn Asn Gln Glu Ala Gly Ala
1               5                   10                  15

Ala Phe Met Gln Phe Leu Thr Leu Leu Gly Asp Val Val Arg Leu Lys
            20                  25                  30

Gly Phe Glu Ser Tyr Arg Ala Gln Leu Asp Thr Lys Thr Asp Ser Thr
```

```
                35                  40                  45
Gly Thr His Ser Leu Tyr Thr Thr Tyr Gln Asp His Glu Ile Met Phe
             50                  55                  60

His Val Ser Thr Met Leu Pro Tyr Thr Pro Asn Asn Gln Gln Gln Leu
 65                  70                  75                  80

Leu Arg Lys Arg His Ile Gly Asn Asp Ile Val Thr Ile Val Phe Gln
                 85                  90                  95

Glu Pro Gly Ser Lys Pro Phe Cys Pro Thr Thr Ile Arg Ser His Phe
            100                 105                 110

Gln His Val Phe Leu Val Val Arg Ala His Ala Pro Cys Thr Pro His
            115                 120                 125

Thr Ser Tyr Arg Val Ala Val Ser Arg Thr Gln Asp Thr Pro Ala Phe
            130                 135                 140

Gly Pro Ala Leu Pro Glu Gly Gly Pro Phe Ala Ala Asn Ala Asp
145                 150                 155                 160

Phe Arg Ala Phe Leu Leu Ala Lys Ala Leu Asn Gly Glu Gln Ala Ala
                165                 170                 175

Gly His Ala Arg Gln Phe His Ala Met Ala Thr Arg Thr Arg Gln Gln
            180                 185                 190

Tyr Leu Gln Asp Leu Ala Thr Asn Glu Val Thr Thr Thr Ser Leu Asp
            195                 200                 205

Ser Ala Ser Arg Phe Gly Leu Pro Ser Leu Gly Gly Arg Arg Ala
210                 215                 220

Thr Pro Arg Ser Pro Gly Ala Asp Val Gln Ala Ala Gly Ala Leu Met
225                 230                 235                 240

(2) INFORMATION FOR SEQ ID NO: 7:

(i) SEQUENCE CHARACTERISTICS:
        (A) LENGTH: 238 amino acids
        (B) TYPE: amino acid
        (C) STRANDEDNESS: single
        (D) TOPOLOGY: linear (xi) SEQUENCE DESCRIPTION: SEQ ID NO: 7:

Gly Gln Thr Ser Glu Glu Glu Leu Phe Ser Thr Asn Glu Glu Ser Pro
 1               5                  10                  15

Ala Phe Val Glu Phe Leu Glu Phe Leu Gly Gln Lys Val Lys Leu Gln
                 20                  25                  30

Asp Phe Xaa Gly Phe Arg Gly Gly Leu Asp Val Thr His Gly Gln Thr
             35                  40                  45

Gly Thr Glu Ser Val Tyr Cys Asn Phe Arg Asn Lys Glu Ile Met Phe
             50                  55                  60

His Val Ser Thr Lys Leu Pro Tyr Thr Glu Gly Asp Ala Gln Gln Leu
 65                  70                  75                  80

Gln Arg Lys Arg His Ile Gly Asn Asp Ile Val Ala Val Val Phe Gln
                 85                  90                  95

Asp Glu Asn Thr Pro Phe Val Pro Asp Met Ile Ala Ser Asn Phe Leu
            100                 105                 110

His Ala Tyr Val Val Gln Ala Glu Gly Gly Pro Asp Gly Pro
            115                 120                 125

Leu Tyr Lys Val Ser Val Thr Ala Arg Asp Asp Val Pro Phe Gly
            130                 135                 140

Pro Pro Leu Pro Asp Pro Ala Val Phe Arg Lys Gly Pro Glu Phe Gln
145                 150                 155                 160
```

```
Glu Phe Leu Leu Thr Lys Leu Ile Asn Ala Glu Tyr Ala Cys Tyr Lys
                165             170             175

Ala Glu Lys Phe Ala Lys Leu Glu Glu Arg Thr Arg Ala Ala Leu Leu
                180             185             190

Glu Thr Leu Tyr Glu Glu Leu His Ile His Ser Gln Ser Met Met Gly
            195             200             205

Leu Gly Gly Asp Glu Asp Lys Met Glu Asn Gly Ser Gly Gly Gly
        210             215             220

Phe Phe Glu Ser Phe Lys Arg Val Ile Arg Ser Arg Ser Gln
225             230             235
```

DNA ENCODING SPA-1PROTEIN

CROSS REFERENCE TO RELATED APPLICATION

This application is a division, of application Ser. No. 08/380,403, filed Jan. 30, 1995, now U.S. Pat. No. 5,831,024, which is a continuation-in-part of application Ser. No. 08/325,909, filed Oct. 19, 1994, now abandoned.

TECHNICAL FIELD

The present invention relates to a SPA-1 protein involved in the control of cell division, and fragments thereof, genes coding therefor as well as antibodies against the protein.

BACKGROUND OF INVENTION

Lymphoid cells have unique properties in cell growth ability in comparison with many other somatic cells. Namely, lymphoid cells, similar to many other somatic cells, are differentiated from a hematopoietic stem cell to mature cells via many steps of cell division, and once enter the interphase (G0/G1). After that if they are stimulated with an antigen or a special growth factor, they again enter to a cell cycle and increase to a clone with a redifferentiation, and then return to the interphase (memory cells). In addition to functional differentiation and expression specific to lymphoid cells, such repeated cell proliferation (clone proliferation) is one of the big factors in an immune response of an organism.

DISCLOSURE OF THE INVENTION

The present invention relates to a novel protein SPA-1 and fragments thereof expected to be involved in the control of said repeated cell growth, and fragments thereof, genes coding therefor, as well as antibodies against said proteins.

BRIEF EXPLANATION OF DRAWINGS

FIG. 1 compares an amino acid sequence of Span-N (SEQ ID No:6) and an amino acid sequence of GAP3m protein (SEQ ID NO:7).

FIG. 2 schematically shows a structure of SPA-1 protein.

DETAILED DESCRIPTION OF THE INVENTION

Figure 3:
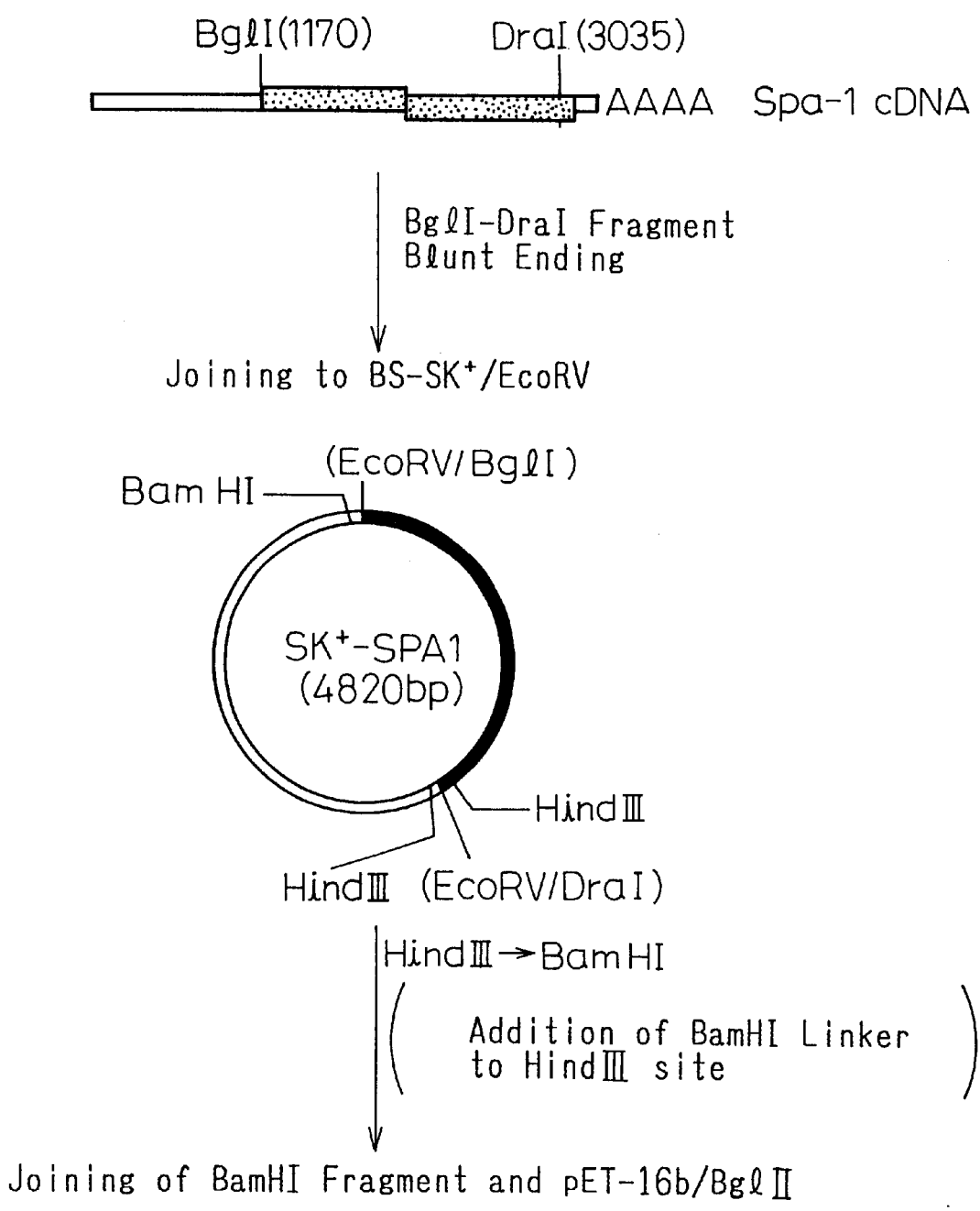
FIG. 3 shows a process for construction of a recombinant expression plasmid for SPA-1 protein.

The present invention relates to a protein which controls a mechanism of cell division and is not expressed in the interphase but is a expressed in the nucleus after entering into a cell cycle, during the cell cycle of a mammalian cell.

This protein is designated SPA-1 and has a structure shown in FIG. 2. Namely SPA-1 comprises the N-terminal half thereof which may be further divided to Span-N positioned on the N-terminal side and having a high homology with GAP3 protein, and Span-C adjacent to the C-terminal of the Span-N and having a unique amino acid sequence.

An amino acid sequence deduced from a nucleotide sequence of cDNA starts with the first Met and ends at the 693rd Ala in SEQ ID NO.: 2. The Span-N has an amino acid sequence starting with the first Met and ends with the 190th Leu, and Span-C has an amino acid sequence starting with the 191st Ala and ends at the 327th Leu of SEQ ID NO: 2.

However, polypeptides and proteins of the present invention are not limited to those described above, but those having small modification in a precise amino acid sequence while maintaining the activities of the present invention are included in the present invention. These modifications include replacement of one or more amino acids in the sequence with other amino acids, and addition or deletion of one or more amino acids, and these variations are included in the present invention as far as they maintain the activities of the present invention.

The addition, deletion and replacement of amino acids can be carried out according to site-specific mutagenesis well known prior to filing the present invention (for example, see Nucleic Acid Research Vol. 10, No. 20, p 6487 to 6500, 1982)), and regarding the addition, deletion and replacement of amino acids, "one or more amino acids" means, for example, those number of amino acids which can be added, deleted or replaced by site-directed mutagenesis.

The above-mentioned polypeptides or proteins can be produced by expressing a gene coding for said polypeptides or proteins according to a genetic engineering procedure. A gene coding for said polypeptides or proteins can be obtained as cDNA, genomic DNA or chemically synthesized DNA.

A cDNA coding for SPA-1 may be obtained from lymphocytes by cloning a gene which is not substantially expressed in the interphase (G0/G1 phase) but is expressed in the growth phase (S phase). For example, cDNA coding for SPA-1 can be obtained by preparing a cDNA preparation from lymphocytes in the G0/G1 phase and a cDNA preparation from lymphocytes in the S phase according to a conventional procedure, allowing these cDNA preparations to hybridize, and selecting cDNA from the S phase, which does not hybridize with cDNAs from the G0/G1 phase. An example of the concrete methods for cloning is described in Example 1(1).

A genomic DNA coding for SPA-1 can be obtained by constructing a genomic DNA library from a target animal, and screening the genomic DNA library using cDNA, for example a full length cDNA obtained as described above. A concrete process for the screening is described in Example 3. For example, a genomic DNA coding for SPA-1 is obtained as a 5.7 kbp BamHI fragment (designated Spa-GC2) and a 6.6 kbp BamHI fragment (designated Spa-GC9) of the genomic DNA.

Figure 5:
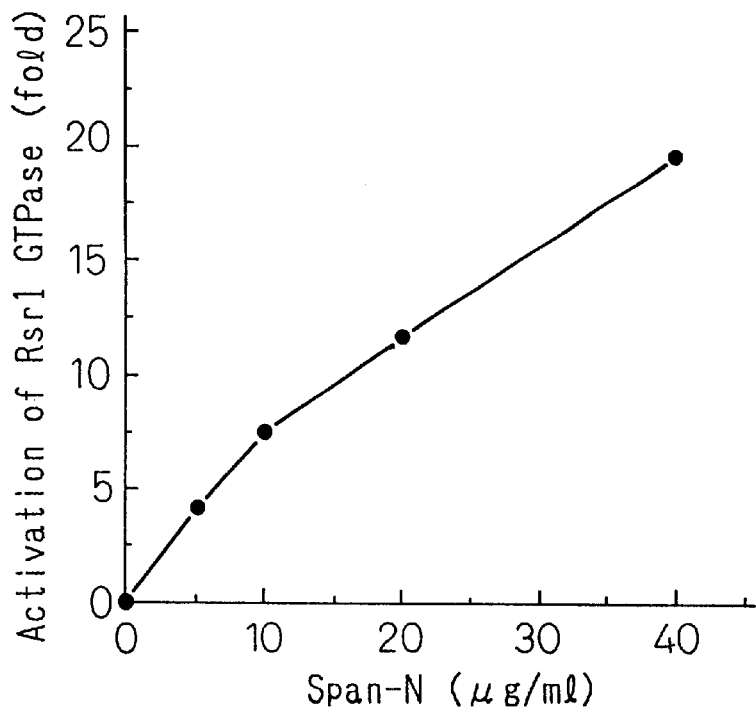
FIG. 5 is a graph showing that Span-N activates Rsrl GTPase in a dose dependent manner.

As shown in FIG. 5 as well as SEQ ID NO: 3, the 5.7 kbp DNA fragment (Spa-GC2) contains 4 exons (exons 1 to 4) which exist in a region of about 2.5 kbp of the 3'-terminal side of the 5.7 kbp fragment. On the other hand, the 6.6 kbp fragment (Spa-GC9) contains 12 dispersed exons (exons 5 to 16) (SEQ ID No:4). These exons 1 to 16 contain a full length of the above-mentioned cDNA. A coding region of the cDNA is contained in a region from the 3'-terminal half of the exon 5 to the 5'-terminal half of the exon 16.

According to the present invention, a DNA coding for SPA-1, or a fragment thereof such as Span-N or Span-C, can be obtained by treating the cDNA or genomic DNA prepared as described above with an exonuclease to eliminate an unnecessary portion, or cleaving the cDNA or genomic DNA with one or more appropriate restriction enzymes followed by supplementing a lacked portion with an oligonucleotide or eliminating a unnecessary portion. In addition, a gene coding for a polypeptide wherein one or more amino acids are lacked in the native amino acid sequence, one or more amino acids are added to the native amino acids sequence, and/or one or more amino acids in the native amino acid sequence are replaced with other amino acids can be obtained by subjecting said cDNA or genomic DNA to, for example, site-directed mutagenesis.

The present invention further includes DNA and RNA hybridizable with one of nucleotide sequences shown in SEQ ID NOs.: 1, 3 or 4. Such a hybridisable DNA or RNA preferably maintains a biological function of SPA-1, or a fragment thereof such as Span-N or Span-C. For example, the hybridisable DNA or RNA is that hybridisable with the above-mentioned cDNA or genomic DNA under the condition of, for example, 50% formamide, 5×SSC, 10% Na-dextran and 20 mM Na-phosphate (pH 6.5) at 42° C.

The present polypeptide or protein can be expressed in eukaryotic cells or prokaryotic cells according to a conventional procedure. The eukaryotic cells include cultured cells such as NIH3T3 cells, Cos-1 cells, CHO cells etc. of human or other animals, as well as enkaryotic microorganisms such as yeast, filamentous fungi. Yeast includes *Saccharomyces cerevisiae*) etc.; the filamentous fungi include the genus Aspergillus, such as *Aspergillus niger* etc. The prokaryotic organisms include bacteria. For example, Bacillus, such as *Bacillus subtilis, Escherichia coli* etc. are used.

To express said DNA in these hosts, an expression vector comprising a DNA containing said coding region, and an expression control region for said DNA is used. The expression control region used in the expression vector can be conventional one. For example, for expression in animal cells, a viral promoter such as LTR promoter, CMV promoter, SRα promoter etc. may be used; for expression in *E. coli*, T7 promoter, LacZ promoter etc. may be used; and as yeast promoter, for example, α-conjugation factor promoter can be used.

The present polypeptides or proteins can be obtained by culturing host cells transformed with an expression vector as described above, and recovering a desired polypeptide or protein from the culture. Transformation of host cells with an expression vector can be carried out depending on the nature of the host cells according to a conventional procedure. Culturing of the transformed cells also can be carried out according to a conventional procedure. Recovery and purification of a desired polypeptide from a culture are carried out according to a combination of conventional procedures used in purification of proteins including affinity chromatography, concentration, lyophilization etc.

EXAMPLES

The present invention is further explained in detail in the following Examples, but the scope of the invention is not limited to that of the Examples.

Example 1
Cloning and Characterization of SPA-1 cDNA
(1) Cloning of SPA-1 cDNA According to the present invention, first, a gene which is little expressed in the quiescent state (G0/G1 phase) but induced in the cycling state (S phase) of lymphocytes, was cloned by differential hybridization between a lymphoid cell line (LFD-14) in the quiescent state by starvation of interleukin 2 (IL-2) for 3 weeks (LFD-14⁻) and those in the cycling state by restimulation of IL-2 (LFD-14⁺). A cDNA library was constructed using poly (A) ⁺RNA prepared from LFD14⁻ in a CDM8 cloning vector according to a conventional procedure (Aruffo, a., et al., Proc. Natl. Acad. Sci. USA, 84, 8573, 1987)). [$\alpha$-$^{32}$P] dCTP-labeled cDNA probes were synthesized from poly (A) ⁺RNA's prepared from LFD-14⁻ and LFD-14⁺. Duplicate filters of the cDNA library were hybridized with each of above cDNA probes in hybridization buffer (5×SSC, 5×Denhardt's solution, 50 μg/ml salmon sperm DNA, 50 mM sodium phosphate, 0.1% SDS) at 65° C. overnight. Filters were washed with 0.1× SSC, 0.1% SDS at 65° C. before autoradiography. A cDNA clone, which was selectively detected by LFD-14⁺ probe, was designated SPA-1 and a vector comprising this cDNA was designated pcSPA-1. The SPA-1 cDNA can be isolated by cleaving said vector with a restriction enzyme Xho I.

(2) Structure of SPA-1 cDNA

The SPA-1 cDNA was sequenced according to a conventional procedure, and a result is shown in SEQ ID NO.: 1. This cDNA is about 3.5 kb in length, and has at the 5'-terminal side a long (about 1.2 kb) 5'-non-translation region containing a lot of short open reading frames (ORFs). This region is a strong translation-repressing region commonly found in certain oncogenes, showing that the SPA-1 gene is also strongly repressed at a level of translation.

This cDNA further comprises an open reading frame of about 2.1 kb starting from the 1200th nucleotide A (adenine) to the 3278th nucleotide C (cytosine) in SEQ ID NO.: 1. Among the amino acid sequence encoded by this open reading frame (SEQ ID NO:2), the N-terminal half (190 amino acid residues) (designated Span-N) has high homology with human Rap1GAP (GAP₃), and the C-terminal half (designated Span-C) has a novel sequence. The homology between the amino acid sequences of Span-N and GAP$_3$ is shown in FIG. 1.

(3) Preparation of Monoclonal Antibodies to Each Domain in SPA-1 N-terminal Portion SPA-1 cDNA was cleaved with a restriction enzymes BglI and PstI to obtain a DNA fragment coding for Span-N and a DNA fragment coding for Span-C (about 140 amino acid residues). On the other hand, pGEX-1 vector (Pharmacia) was cleaved with PstI, blunt-ended using T$_4$ polymerase and EcoRI linkers were added to the blunted ends. The above-mentioned Span-N DNA fragment or Span-C DNA fragment was inserted into the EcoRI sites of the modified pGEX-1 vector to construct an expression plasmid pGEX-SpanN or pGEX-SpanC comprising a sequence coding for a fusion protein of the Span-N or Span-C and GST (glutathione-S-transferase), respectively. These expression plasmids were expressed in *E. coli*, and expression products were recovered and purified to obtain Span-N/GST fusion protein and Span-C/GST fusion protein respectively.

Then 200 μg of the fusion protein was mixed with Freund's complete adjuvant and the mixture was subcutaneously administered to immunize an Arumenia hamster (male, 5 weeks old). After that, 200 μg each of the fusion protein mixed with Freund's incomplete adjuvant was three times intraperitoneally administrated to the hamster, at intervals of two weeks. After three days from the final immunization, the spleen was removed from the hamster, and minced to prepare a single cell suspension of the spleen.

This suspension was subjected to a cell fusion with mouse myeloma cell line P3U1, according to the Leo, 0 et al. method (Proc. Natl. Acad. Sci. USA, 84: 1374, 1984), to obtain hybridomas.

Among the hybridomas, clones producing a desired antibody were selected with ELISA using corresponding fusion protein used to immunize the hamster. Namely, 1 μg/well of each fusion protein (GST-SpanN, or GST-SpanC) or 1 μg/well of GST protein alone was immobilized to a 96-well plate, and 100 μl of hybridoma supernatant was added into each well and allowed to react with the immobilized protein.

Figure 7:
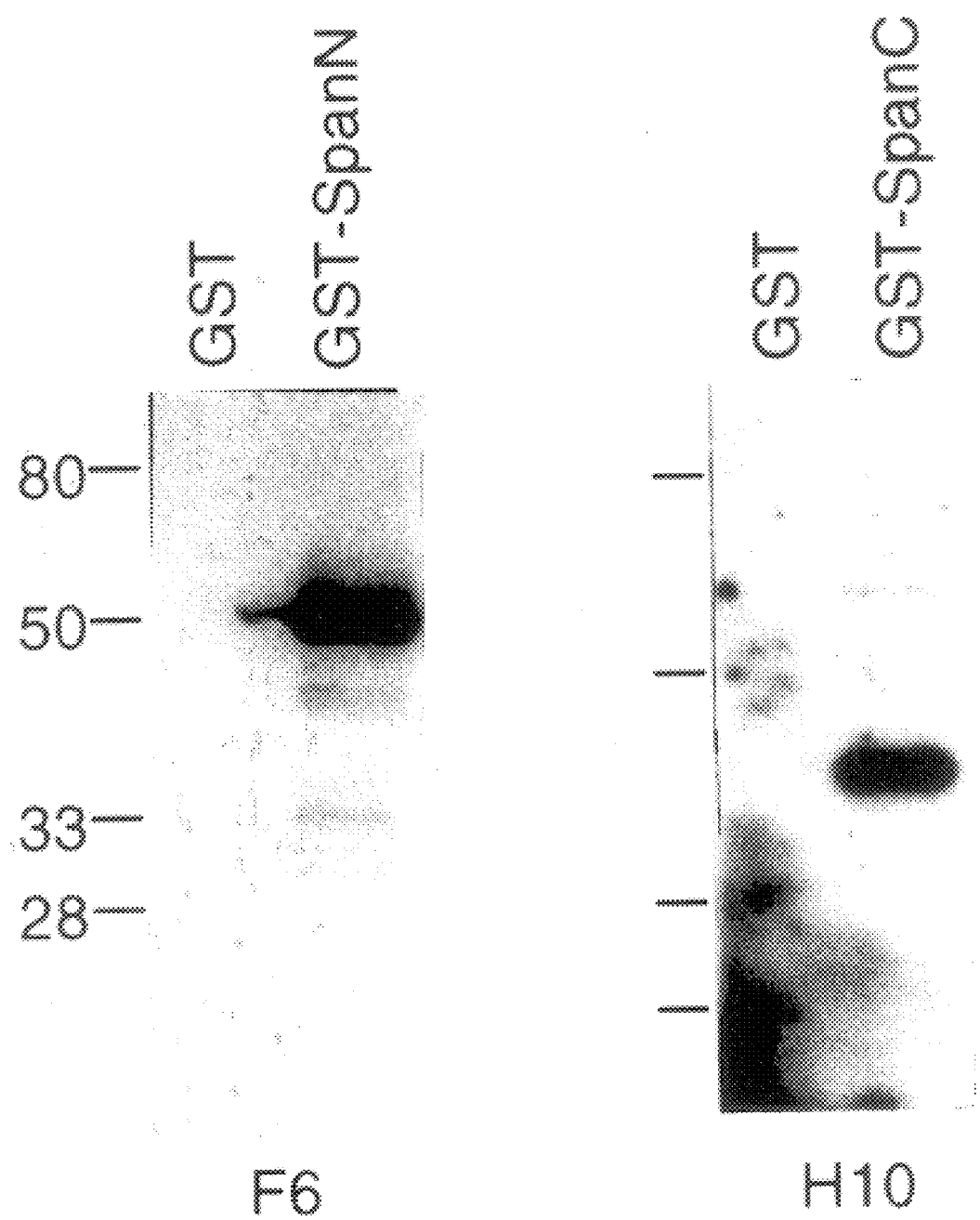
FIG. 7 shows a result of an electrophoresis showing the reactivity of monoclonal antibodies F6 and H10 to GST protein, GST-Span N and GST-Span C fusion proteins.

Then, anti-hamster IgG-peroxidase was added to the wells for reaction, followed by a substrate ABTS (2,2'-adino-di-3-ethyl-benzothianodino-6-sulfate) for coloring, and clones which react with the fusion protein but do not react with GST were selected as positive clones. Cells in the positive wells were cloned by limiting dilution method to obtain a clone from a single cell. A monoclonal antibody against Span-N is designated "F6", and monoclonal antibody against Span-C is designated "H10". FIG. 7 shows reactivity of each monoclonal antibody with fusion proteins, analyzed by Western blotting.

Namely, FIG. 7 shows a result obtained by the following method: 10 μg of GST-SpanN or GST-SpanC fused protein, or GST alone was separated by SDS-PAGE, blotted on a membrane, reacted with an F6 or H10 antibody solution (10 μg/ml), and detected with $^{125}$I-Protein A (Amersham).

Note, the hybridoma producing monoclonal antibody F6 was designated F6 and deposited with National Institute of Bioscience and Human-Technology Agency of Industrial Science and Technology as FERM BP-4839 on Oct. 18, 1994 under the Budapest treaty; and the hybridoma producing monoclonal antibody H10 was designated H10 and deposited with the National Institute of Bioscience and Human-Technology Agency of Industrial Science and Technology as FERM BP-4840 on Oct. 18, 1994, under the Budapest treaty.

(4) Detection of SPA-1 Protein by Monoclonal Antibody

Protein was extracted from cultured cells of lymphoid cell line LFD14 (Kubota, H. et al., J. Immunol. 145, 3924, 1990) according to a method of Harlow, E. et al., Mol. & Cellular Biology 6: 1579, 1986), and identified by immunoblotting using said monoclonal antibodies, immunoprecipitation method, immunostain method etc.

As a result, for example, a protein from lymphoid cell line LFD14 was detected as a band of a molecular weight of about 68 KDa in Western blotting using monoclonal antibody F6. From this result, it is expected that the SPA-1 gene encodes a nuclear protein of about 68 KDa.

Namely, it is expected that SPA-1 protein of the present invention has an amino acid sequence starting from the first amino acid methionine and ending at the 693rd amino acid alanine in SEQ ID NO: 1.

Example 2

Expression of SPA-1 cDNA (1) Expression of SPA-1 Protein

Expression by in vitro transcription/translation

Figure 8A:
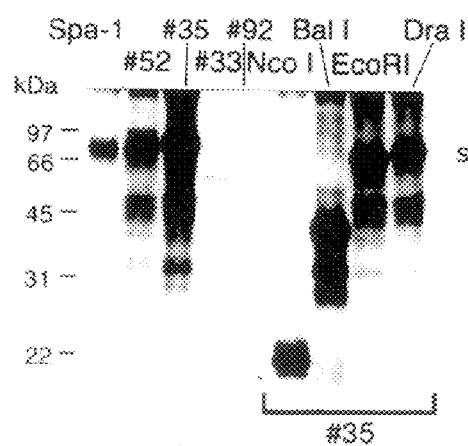
FIG. 8 shows a result of an electrophoresis showing a profile of expression products from SPA-1 genes lacking various regions.
Figure 8B:
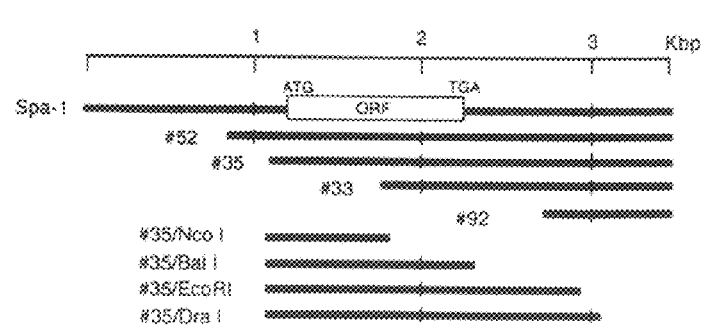

FIG. 8 shows a result of an analysis of SPA-1 protein expressed by in vitro transcription/translation method using various lengths of SPA-1 cDNA as a template. As shown in FIG. 8, pBluescript Ks$^+$-SPA-1 plasmid containing a full length SPA-1 cDNA, clones (#52, #35, #33, and #92) lacking 5'-terminal portion of said SPA-1 cDNA in different length, and plasmids containing a full length ORF but lacking 5'-non-translational region which negatively acts on the translation upwards from the different positions (NcoI (1928), BalI (2229), EcoRI (2879), or DraI (3035)) downstream of the plasmid #35 were used as a template.

Using 10 μg of these template DNAs, complementary mRNAs (cRNAs) were synthesized with an RNA transcription kit (Stratagene). These cDNAs were in vitro translated in the presence of $^{35}$S-methionine (Amersham) according to the Tagawa et al. method (J. Biol. chem. 256: 20021, 1990) using an in vitro expression translation kit (Promega). The translation product was immunoprecipitated with the above-mentioned H10 antibody and protein A beads (Pharmacia), and the precipitate was analyzed by SDS-PAGE.

As a result, where full length pBluescript-KS$^+$-SPA-1, #52 and #35 plasmids completely containing ORF and 3'-non-translational region were used as templates, a specific band of about 85 KDa was detected, while where plasmid (#33) lacking a part of the ORF was used a translation product shortened (about 50 KDa) corresponding to the lack of the ORF was detected. In addition, where plasmids (#35/BalI, #35/EcoRI, and #35/DraI) lacking 3'-non-translation region were used, translation products shorter than 85 kDa corresponding to an extent of lacking were obtained.

These results show that the SPA-1 protein is a polypeptide starting from the first amino acid methionine and ending at the 693rd amino acid alanine encoded by a nucleotide sequence started with the 1200th nucleotide A and ending at the 3278th nucleotide C in SEQ ID NO: 1.

Expression by stable animal cell transfectant

The SPA-1 cDNA was obtained by cleavage of plasmid SPA-1 with restriction enzymes BglI and DraI, and inserted into EcoRI site of pSRa expression vector (Takebe, Y. et al., Mol. Cell Biol., 8: 466–472, 1988) to construct an expression plasmid SRα-SPA-1, which was then co-introduced into NIH3T3 cells (ATCC CRL-1658) together with a plasmid pSV$_2$NeO and transfected cells were selected by G418 to obtain a stable transfectant (NIH/SPA-1 cells).

Figure 9A:
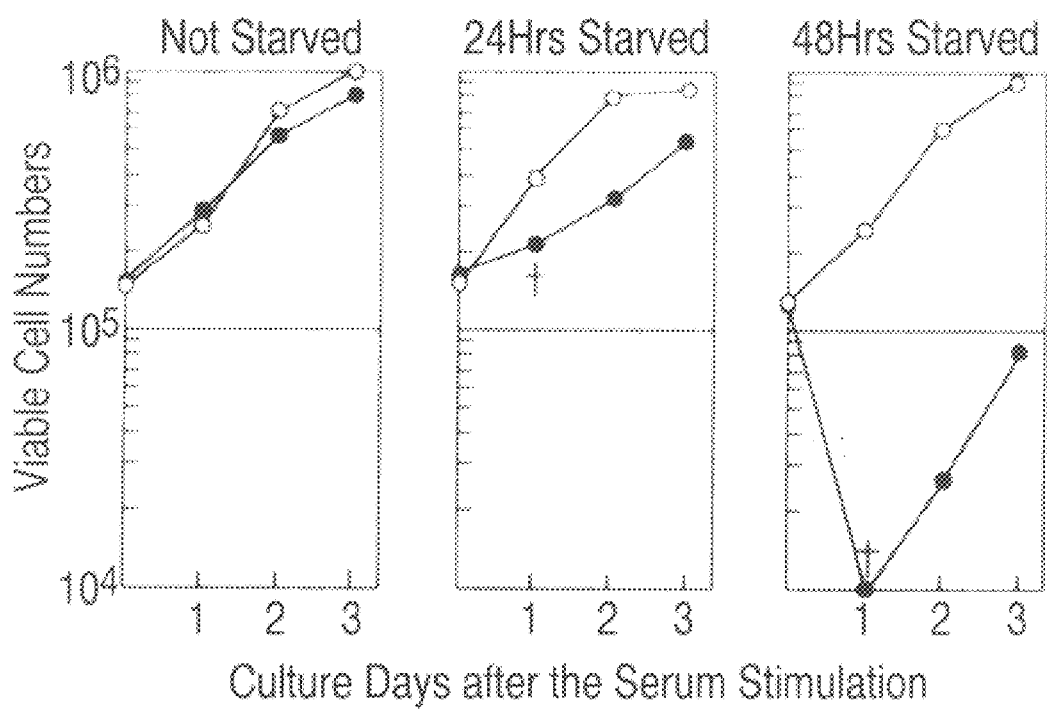
FIGS. 9a and 9b are micrographs showing the effects of the overexpression of SPA-1 gene in an animal cells on the cell growth when the growth of said animal cells is synchronized by serum-starvation and addition of serum.
Figure 9B:
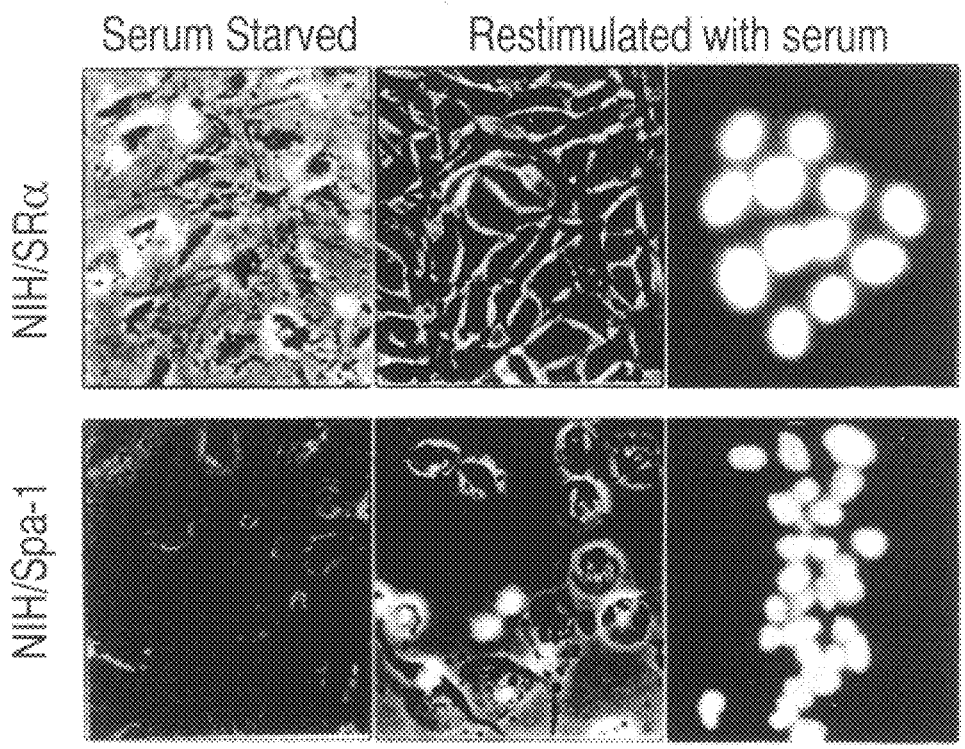
Figure 10A:
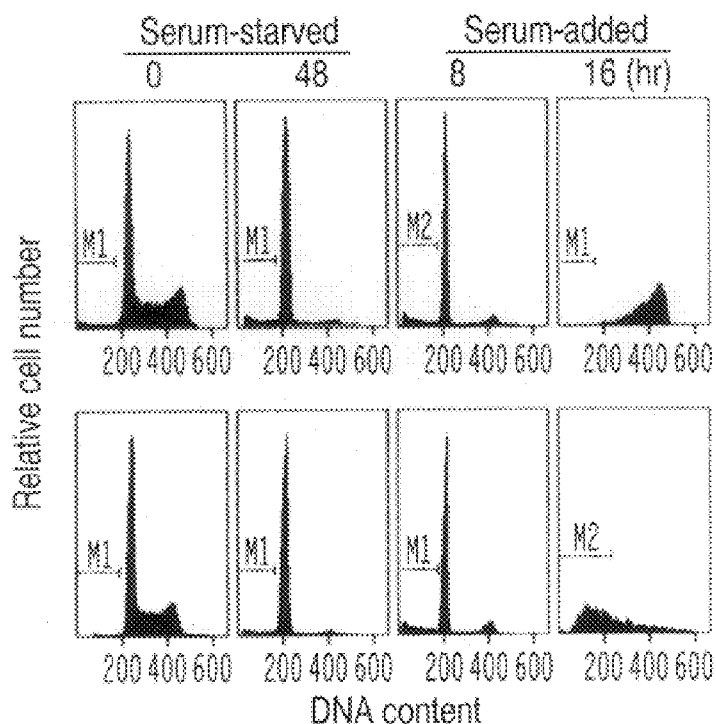
FIGS. 10a, b and c are micrograph showing the effects of overexpression of a SPA-1 gene introduced into animal cells on the cell growth when the growth of said animal cells is synchronized by serum-starvation and addition of serum.

As shown in FIG. 9A, the NIH/SPA-1, cells grew under a usual culture condition (supplemented with 5% serum) in a manner not different from control cells, i.e., NIH3T3 cells to which SRα vector alone had been introduced do. However if the same cells were cultured in a serum-reduced condition (0.5% serum) to synchronize them to the G1 phase (extended G1) and after a certain time later the cells were restimulated with serum to reenter the cell cycle, they rapidly died off in the middle to end of the S phase (FIG. 10A). Morphologically, the cells became round up, and remarkable nuclear condensation was observed, and therefore it was considered that so-called mitotic catastrophes occurred (FIG. 9B). In addition, SPA-1 exhibits a unique change of expression along with synchronization of cell cycle, suggesting that expression thereof, similar to cyclines, is controlled by cell cycle (FIGS. 10, B and C).

FIG. 9 shows induction of the death of cells by growth stimulation after blocking the G$_1$ phase of cell cycle, in NIH3T3 cells (NIH/SPA-1) transfected with SPA-1 cDNA. FIG. 9A shows a result obtained by culturing the NIH/SPA-1 cells (●) and the NIH-SRα cells (○) prepared by introducing pSRα vector alone into NIH3T3 cells in the presence of 5% serum to an almost confluent state, transferring the cells to a medium containing 0.5% serum, and after culturing the cells for 0, 24 or 48 hours, transferring the cells to a medium containing 20% serum so as to count the number of cells as time elapses.

FIG. 9B shows micrographs of NIH/SRα cells and NIH/SPA-1 cells cultured in the presence of 0.5% serum for 48 hours and then in the presence of 20% serum for 18 hours. The right shows the morphology of the nucleus of the cell at that time, in Hoechst 33427 (Sigma). The shrink of the nucleus was observed in NIH/SPA-1.

Figure 10B:
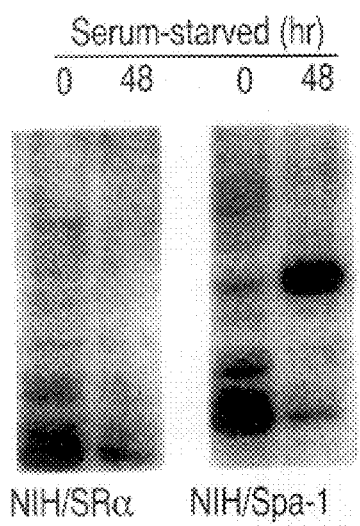

In FIG. 10, A shows a result of analysis of cell cycle in NIH/SPA-1; the upper portion relates to NIH/SRα cells and the lower portion relates to NIH/SPA-1 cells. After 16 hours from the addition of serum, NIH/SPA-1 cells had died (control cells had entered to the S phase). FIG. B shows an accumulation of SPA-1 protein in a serum-free culture ($G_1$ arrest). For NIH/SPA-1 cells, although the transfected SPA-1 mRNA was detected, under a usual condition (lane of oh) SPA-1 gene was not substantially detected by Western blotting (probably due to constant degradation). However, where a serum concentration was reduced to 0.5% to maintain the cell cycle at the $G_1$ phase ($G_1$ arrest), accumulation of SPA-1 protein was observed.

Figure 10C:
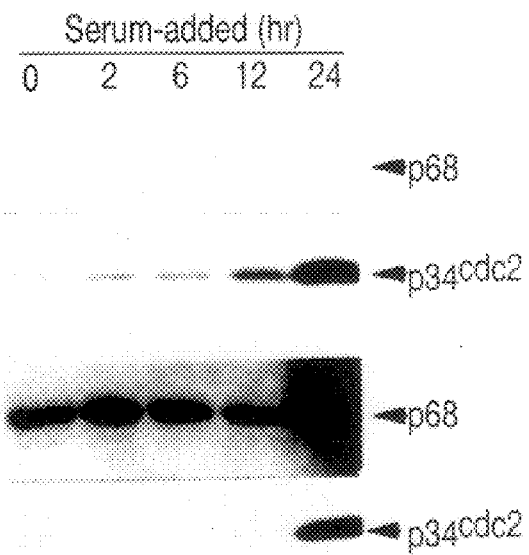

FIG. 10C shows the kinetic change of SPA-1 protein after the addition of serum. After the $G_1$ arrest for 48 hours, the cell cycle was started by the addition of serum, then only living cells were recovered at each time and SPA-1 protein was detected. A part of NIH/SPA-1 cells survived after the addition of serum for 24 hours, and in these cells the increase of cαc2 expression was observed. On the other hand, at this point, SPA-1 protein had already decreased.

Expression of recombinant SPA-1 in E. coli

The SPA-1 cDNA was cleaved with a restriction enzyme BglI (which cleaves at the 1171st nucleotide) and a restriction enzyme DraI (which cleaves at the 3038th nucleotide) to obtain a BglI-DraI fragment, which was then blunt-ended with T4 polymerase. This DNA fragment was ligated to EcoRV-cleaved plasmid BS-SK (Transgene) to obtain a plasmid SK$^+$-SPA-1. Next, this plasmid was cleaved with Hind III, and to the resulting Hind terminals were added BamHI linkers, and the BamHI linkers were cleaved with BamHI to obtain a BamHI fragment, which was inserted into BglII-digested expression plasmid pET-16b (Novagen, USA) to obtain an expression plasmid pET-SPA1. This plasmid was used to transform E. coli.

By culturing the E. coli, subjecting an expression product from the culture to electrophoresis, and detecting the product by the above-mentioned monoclonal antibody F6, a band corresponding to a molecular weight of 85 KDa was detected and expression of recombinant SPA-1 (rSPA-1) was confirmed.

A process for construction of the expression plasmid pET-SPA-1 is shown in FIG. 3.

(2) Physiological Activities of Span-N

Since Span-N has homology with GAP3, GAP activity of the above-mentioned GST-SpanN fusion protein was tested. As a control, a fusion protein of human GAP3 (75th to 663rd amino acid residues) and GST was used. The effects of these fusion proteins on GTPase activity of yeast Rsr1 (1st to 272nd residues), human Rap1A (Glu$^{63}$) (1st to 184th residues), human Ha-Ras (1st to 189th residues) and a human RhoA (1st to 193 residues) GST fusion protein (Nur-E-Kamal et at., Mol. Biol. Cell 31, 1437–1442, 1992; Nur-E-Kamal et al., J. Biol. Chem. 267, 1415–1418, 1992) was investigated according to the Maruta et al. method (J. Bio. Chem. 266: 11661–11668, 1991). As a result, it was shown that although the Span-N was not effective to Ha-Ras, Rac1, Rho1 etc., it has selective GAP activity to Rap1 and Rsr1.

TABLE 1

Activation of GTPase activity of Rsr1, Rap1, etc. by Span-N or GAP3m

| smG Protein | Native GTPase activity (Turn over/min.) | Stimulation (times) | |
|---|---|---|---|
| | | Span-N | GAP3m |
| Rsr1 | 0.001 | 16.0 | 7.0 |
| Rap1A(Glu$^{63}$) | 0.0015 | 6.0 | 10.0 |
| Ha-Ras | 0.022 | 0.3 | 0 |
| RhoA | 0.060 | 0.6 | 0 |
| Rac1 | 0.090 | 0 | |

Figure 4:
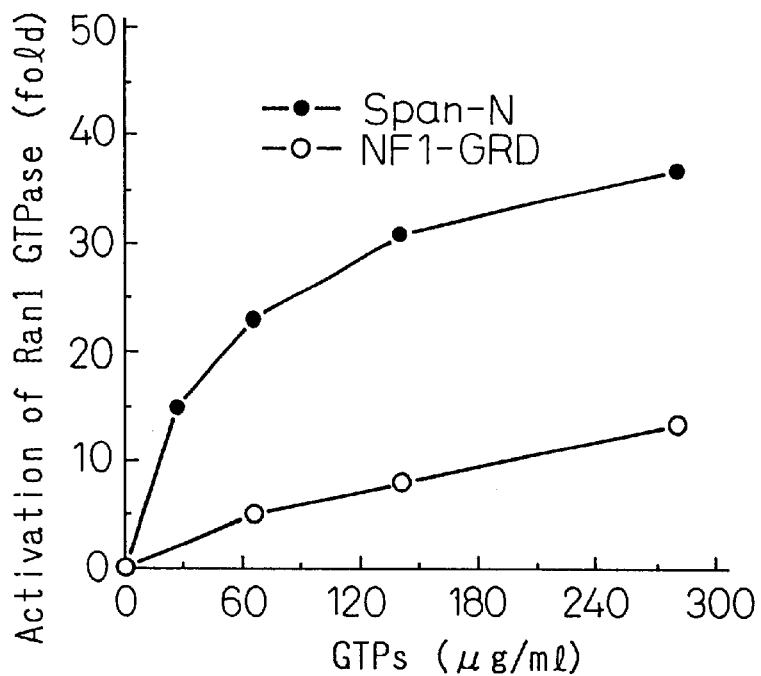
FIG. 4 is a graph showing that Span-N activates Ran1 GTPase in a dose dependent manner.

In addition, the relationship between Span-N concentration and Rsr1 GTPase activity is shown in FIG. 4. The Figure shows that Rsr GAP activity of Span-N depends on its concentration. Note that GAP activity was measured according to the Maruta et al. method (J. Biol. Chem. 266: 11661–11668, 1991).

SPA-1 is a nuclear protein, while there is no report that Rap1 exists in the nucleus. Therefore, activity of Span-N etc. to the sole low molecular weight G protein, Ran, known to be present in nucleus was studied. As a result, it was shown that Span-N exhibits a clear GAP activity on Ran. This result is shown in Table 2.

TABLE 2

Activation of Ran GTPase by Span-N and other GAPSs

| GAPs | EC$_{16}$ (μg/ml) |
|---|---|
| SPA-1(Span-N) | 25 |
| GAP3m(Rap GAP) | 130 |
| p190C(Rho GAP) | 150 |
| NF1-GDR(Ras GAP) | 300 |

In addition, FIG. 5 shows the relationship between Span-N concentration and Ran GTPase activity.

Example 3

Cloning of Genomic Gene (1) A mouse genomic library (EMBL3-Adult DBA/2J liver DNA:CLONTECH, ML 1009d) comprising 1.0×10$^6$ clones was blotted on Hybond-N$^+$ membranes (Amersham, RPN 303B). A vector SPA-1 cDNA/pBluescript incorporating a SPA-1 cDNA was cleaved with XhoI (Toyobo, XHO-101) to obtain a full length SPA-1 cDNA, which was then labeled with α$^{32}$P-dCTP (Amersham, PB0205) using a Nick Translation Kit (Amersham, N5000).

This probe was reacted with the above-mentioned genomic library in the presence of Rapid Hybridization Buffer (Amersham, RPN1636). As a primary screening, 15 positive or pseudopositive signals were obtained. As a secondary screening 9 positive clones were obtained. These were further screened so as to confirm all of the 9 strains were cloned. Genomic DNA in these clones are designated GC1 to GC9, respectively.

(2) Preparation of Mouse Total DNA

First 2 cm of the tail of a Bal b/c mouse of 4 weeks old was cut off, and was put into 1.5 ml Epptendolf tube. Then the cut tail was sliced with scissors. In this tube were added 500 μl of a mixed solution (439 μl of 1×SSC, 5 μl of 1M Tris-HCl (pH 7.5) and 1 μl of 0.5M EDTA (pH 8.0)), 50 μl of 10% SDS, and 5 μl of 20 mg/ml proteinase K, and the mixture was incubated at 37° C. for 12 hours.

Next, 500 μl of buffered phenol was added thereon, and the whole was gently mixed for 5 minutes. The mixture was centrifuged at 10,000 rpm, at a room temperature for 5 minutes. The liquid phase was transferred into a fresh Epptendorf tube, and 700 µl of isopropanol was added thereon, and the tube was reversed a few times to generate fibrous precipitate.

This precipitate was transferred to a fresh tube into which 500 µl of 70% ethanol had been introduced, and after removing the 70% ethanol, the precipitate was washed with 100% ethanol. The precipitate was dried with dry air and 100 µl of TE buffer was added thereon to prepare a total DNA.
(3) Screening of Genomic DNA Coding for SPA-1

The total DNA prepared in the section (2) was cleaved with BamHI (Toyobo, BHA 102) or EcoRI (Toyobo, ECO-101), blotted on Hybond-N⁺ membranes, and screened by hybridization with the full length SPA-1 cDNA probe prepared in the above section (1). The hybridization was carried out in Rapid Hybridization Buffer as described in the section (1).

As a result, 5.7 kb and 6.6 kb BamHI fragments as well as 9.2 kb, 5.2 kb and 1.4 kb EcoRI fragments were positive. The 5.7 kb and 6.6 kb BamHI fragments contained a full length of SPA-1 cDNA and corresponded to the above-mentioned genomic fragments Spa-GC2 and Spa-GC9. Phage vectors comprising these genomic fragments were designated Spa-GC2/EMBL-3 and Spa-GC9/EMBL-3, respectively.
(4) Sequencing These viral vectors were prepared and cleaved with BamHI, and using a Gene Clean Kit (Funakoshi) a 5.7 kb BamHI fragment from Spa-GC2/EMBL-3 and a 6.6 kb BamHI fragment from Spa-GC9/EMBL-3 were prepared respectively.

Next, each of these fragments was inserted into pBluescript II SK(+) (Toyobo SC212205) at its BamHI site using a DNA Ligation Kit (Takara 6021) and subcloned. Then deletion mutants were prepared by Kilo-Sequence Deletion Kit (Takara, 6030), and sequencing was carried out using a 7-deaza Sequenase (Toyobo, US 70777). As a result, it was founded that the Spa-GC2 contains exons 1 to 4 in its 3'-terminal half, and the Spa-GC9 contains dispersed exons 5 to 16.

Exon 1 extends from base pair number 3109 through base pair number 3284 of SEQ ID NO:3. Exon 2 extends from base pair number 3764 through base pair number 4555 of SEQ ID NO:3. Exon 3 extends from base pair number 5147 through base pair number 5273 of SEQ ID NO:3. Exon 4 extends from base pair number 5354 through base pair number 5524 of SEQ ID NO:3.

The nucleotide sequence of Spa-GC2 is shown in SEQ ID NO.: 3, and the nucleotide sequence of Spa-GC9 is shown in SEQ ID NO.: 4. In the Spa-GC9, an amino acid coding region in cDNA is contained in a region from the 3'-terminal half of the exon 5 to the 5'-terminal half of the exon 16(SEQ ID NO: 5).

Figure 6:
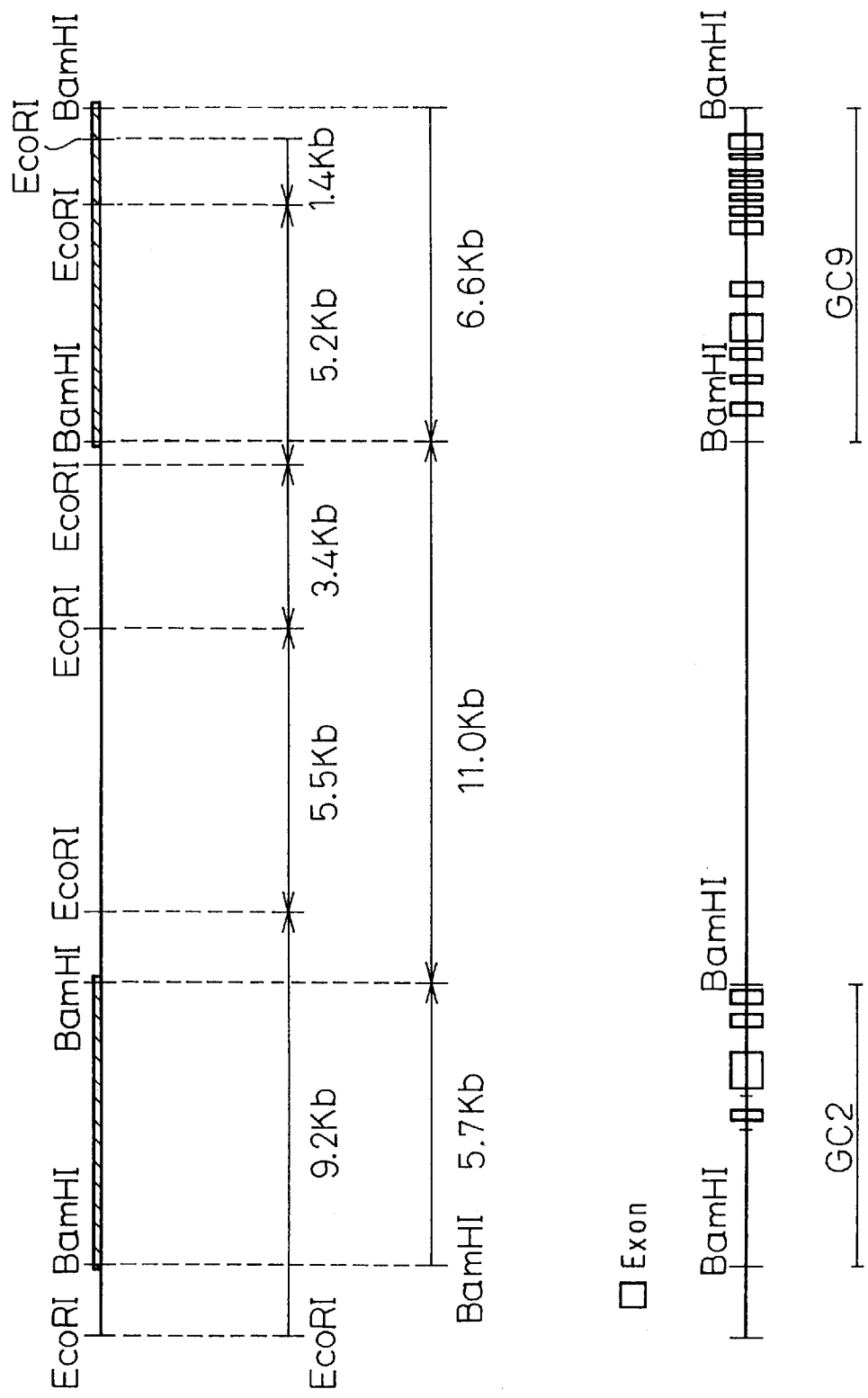
FIG. 6 shows a restriction enzyme map of a genomic DNA coding for SPA-1 of the present invention.

Note that FIG. 6 shows relative positions of the genomic fragments including Spa-GC2 and Spa-GC9.

It was suggested that the SPA-1 protein participates in the regulation of DNA replication and cell division because the protein strongly expressed after the S phase in the cell cycle of normal lymphocyte. On the other hand, it was shown that the said protein contains a Ran GAP activity domain at its N-terminal portion. The Ran is the sole low molecular weight G protein present in the nucleus and is associated with RCC-1 which is a GDP-GTP exchanger of Ran GTPase. RCC-1 is a nuclear protein well conserved in all cells from yeast to mammal, and is well known as a protein participating in check mechanism of entering into the $G_2$/M phase (namely, prevention of premature cell division prior to completion of DNA replication). In addition, recently it has been found that the RCC-1 gene precipitates in various aspects of cell nucleus functions including initiation of DNA replication, extranuclear transport of RNA, etc.

The RCC-1/Ran system is, however, constitutionally expressed regardless of the cell cycle. Accordingly, for long time, an intervention of a cell cycle-dependent factor, especially GAP molecule as an entity which links the cell cycle and RCC-1/Ran is expected. However, its true entity has not been clear. The finding in the present invention strongly suggests that SPA-1 is in fact the intervenient entity. In addition, it was found in the present invention that an over-expression of SPA-1 causes the mitotic catastrophes. This finding suggests that SPA-1 is a central molecule responsible for cell cycle-dependent control of the RCC-1/Ran system.

A mechanism by which the SPA-1 micro-regulates the RCC1/Ran system which represses cyclin/cdc 2 system driving DNA synthesis and cell division is an important object to be solved in future. Especially, the fact that the SPA-1 is highly expressed in lymphoid cells having unique cell growth properties suggests that the SPA-1 plays an important role in a growth control of the lymphoid cells and checking mechanism thereof.

Accordingly, the present protein is promising as differentiation control agent of lymphocytes. In addition, the present protein may be useful as an anti-tumor agent because if the present protein is expressed in tumor cells, it may induce the death of cells at the S phase of the cell cycle.

What is claimed is:

1. An isolated DNA coding for a cell division mechanism controlling protein which is not expressed during interphase ($G_0/G_1$) of the cell cycle but is expressed in the nucleus during cell division, wherein said DNA hybridizes with a nucleotide sequence complementary to SEQ ID NO: 1 in the presence of 50% formamide and 5×SSC at 42° C.

2. An expression vector comprising a DNA according to claim 1.

3. A host transformed with an expression vector according to claim 2.

4. A process for production of a cell division mechanism controlling protein, comprising the steps of:
   culturing a host according to claim 3, and
   recovering the protein from the culture.

5. An isolated DNA coding for a cell division mechanism controlling protein consisting of the amino acid sequence from the first Met to the 693rd Ala of SEQ ID NO: 2.

6. An expression vector comprising a DNA according to claim 5.

7. A host transformed with an expression vector according to claim 6.

8. A process for production of a cell division mechanism controlling protein, comprising the steps of:
   culturing a host according to claim 7, and
   recovering the protein from the culture.

9. An isolated DNA coding for Span-N protein consisting of the amino acid sequence from the first Met to the 190th Leu of SEQ ID NO: 2.

10. An expression vector comprising a DNA according to claim 9.

11. A host transformed with an expression vector according to claim 10.

12. A process for production of Span-N protein, comprising the steps of:
   culturing a host according to claim 11, and recovering the protein from the culture.

13. An isolated DNA coding for Span-C consisting of the amino acid sequence from the 191st Ala to the 327th Leu of SEQ ID NO: 2.

14. An expression vector comprising a DNA according to claim 13.

15. A host transformed with an expression vector according to claim 14.

16. A process for production of Span-C protein, comprising the steps of:
   culturing a host according to claim 15, and
   recovering the protein from the culture.

17. An isolated genomic DNA coding for a cell division controlling protein wherein the genomic DNA consists of the 904th nucleotide to 5741st nucleotide of SEQ ID NO: 4.

18. An expression vector comprising a DNA according to claim 17.

19. A host transformed with an expression vector according to claim 18.

* * * * *